(12) United States Patent
Rajagopal et al.

(10) Patent No.: US 10,052,081 B2
(45) Date of Patent: Aug. 21, 2018

(54) ENHANCED STETHOSCOPE DEVICES AND METHODS

(71) Applicant: California Institute of Technology, Pasadena, CA (US)

(72) Inventors: Aditya Rajagopal, Irvine, CA (US); Alaina Ann Brinley Rajagopal, Irvine, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/678,789

(22) Filed: Aug. 16, 2017

(65) Prior Publication Data

US 2018/0049716 A1 Feb. 22, 2018

Related U.S. Application Data

(60) Provisional application No. 62/376,300, filed on Aug. 17, 2016.

(51) Int. Cl.
| | |
|---|---|
| *A61B 7/04* | (2006.01) |
| *A61B 5/0205* | (2006.01) |
| *A61B 8/00* | (2006.01) |
| *A61B 5/00* | (2006.01) |
| *A61B 5/145* | (2006.01) |
| *A61B 5/08* | (2006.01) |
| *A61B 5/021* | (2006.01) |

(52) U.S. Cl.
CPC .............. *A61B 7/04* (2013.01); *A61B 5/0022* (2013.01); *A61B 5/02055* (2013.01); *A61B 5/726* (2013.01); *A61B 5/7257* (2013.01); *A61B 5/7264* (2013.01); *A61B 8/4477* (2013.01); *A61B 5/021* (2013.01); *A61B 5/0816* (2013.01); *A61B 5/14532* (2013.01); *A61B 5/14542* (2013.01); *A61B 2560/0214* (2013.01)

(58) Field of Classification Search
CPC ... A61B 5/0022; A61B 5/02055; A61B 5/021; A61B 5/0816; A61B 5/14532; A61B 5/14542; A61B 5/7257; A61B 5/726; A61B 5/7264; A61B 7/04; A61B 8/4477; A61B 2560/0214
See application file for complete search history.

(56) References Cited

U.S. PATENT DOCUMENTS

| | | | |
|---|---|---|---|
| 4,413,629 | A | 11/1983 | Durley, III |
| 4,972,841 | A | 11/1990 | Iguchi |
| 5,394,880 | A | 3/1995 | Atlee, III |
| 5,798,489 | A | 8/1998 | Gillio |
| 5,960,089 | A | 9/1999 | Bouricius et al. |

(Continued)

OTHER PUBLICATIONS

International search report and written opinion dated Oct. 12, 2017 for PCT Application No. US-2017047204.

*Primary Examiner* — Mark Fischer
(74) *Attorney, Agent, or Firm* — Wilson, Sonsini, Goodrich & Rosati

(57) ABSTRACT

An enhanced stethoscope device and method for operating the enhanced stethoscope are provided. The enhanced stethoscope device generally operates by providing stethoscope sensors, ultrasonic sensors, and other sensors to obtain a series of measurements about a subject. The series of measurements may be correlated, such as by machine learning, to extract clinically relevant information. Also described are systems and methods for ultrasonic beamsteering by interference of an audio signal with an ultrasonic signal.

29 Claims, 20 Drawing Sheets

(56) References Cited

U.S. PATENT DOCUMENTS

| | | |
|---|---|---|
| 6,106,472 A | 8/2000 | Chiang et al. |
| 7,024,001 B1 | 4/2006 | Nakada |
| 8,939,251 B2 | 1/2015 | Ting |
| 9,078,571 B2 | 7/2015 | Bridger et al. |
| 2006/0241482 A1 | 10/2006 | Karasawa |
| 2007/0088346 A1 | 4/2007 | Mirizzi et al. |
| 2008/0228095 A1 | 9/2008 | Richardson |

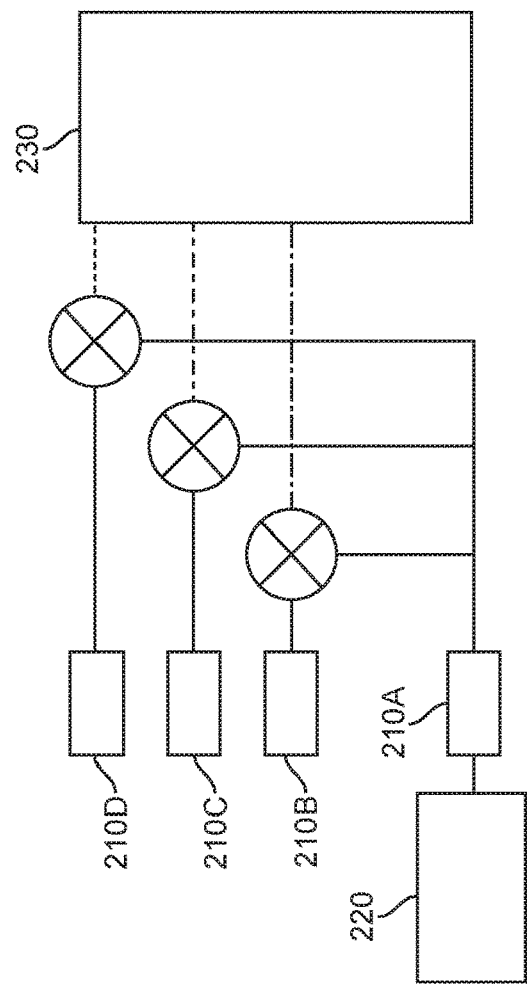
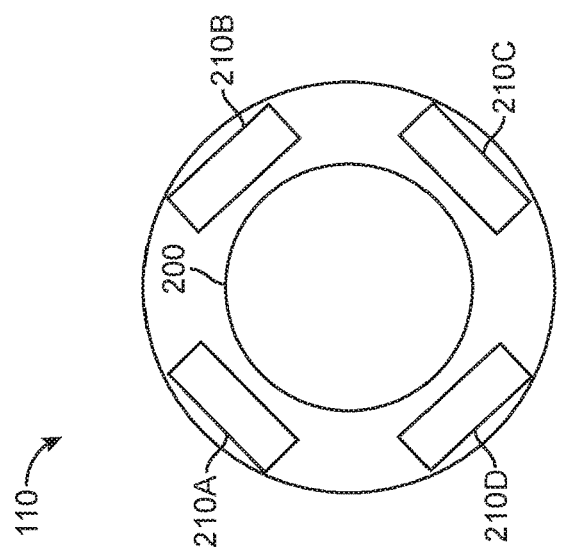
FIG. 2B
FIG. 2A

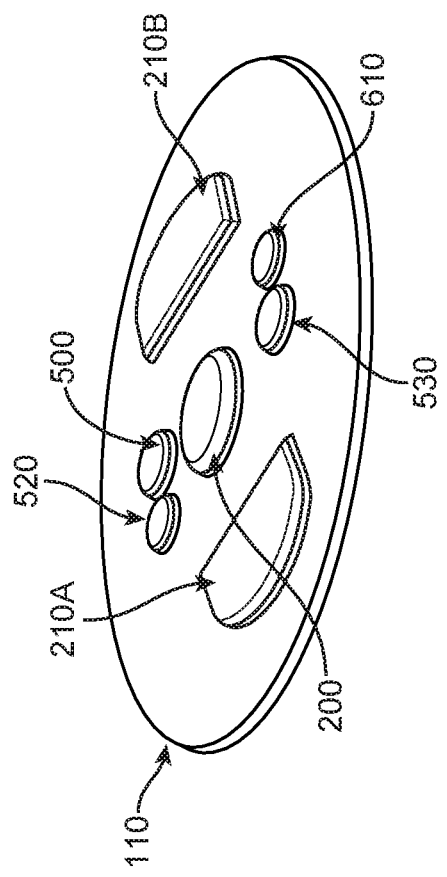
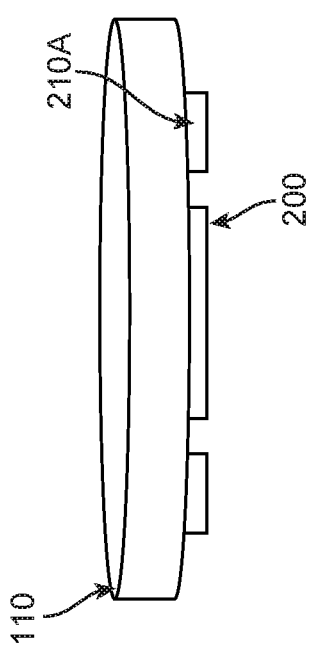
FIG. 5B
FIG. 5A

ENHANCED STETHOSCOPE DEVICES AND METHODS

CROSS-REFERENCE

This application claims the benefit of U.S. Provisional Application No. 62/376,300, entitled "Enhanced stethoscope device, method, and platform for measurement of physiology", filed Aug. 17, 2016, which application is incorporated herein by reference in its entirety for all purposes.

BACKGROUND

The traditional stethoscope is ubiquitously used in the chain of medical care. However, in isolation it is only capable of assessing respiration and heart rate; blood pressure measurements are possible when the stethoscope is used in conjunction with a sphygmomanometer. A traditional stethoscope head contains a diaphragm that mechanically amplifies audio signals in the 0.01 Hz to 3 kHz range. For medical use, operators fix the head of the stethoscope adjacent to the phenomenon being observed (e.g. against the chest to measure respiration). The diaphragm transmits the sound coupled into the stethoscope head from the features (such as the heart or lungs) into a set of ear pieces. The operator then interprets this sound and manually records this measurement. Studies have shown that these measurements have a strong dependence on the level of training for the operators, as well as the audio environment in which the measurements are taken.

Electronic stethoscopes have attempted to address the limitations of traditional stethoscopes in loud environments, such as the emergency department. They convert the mechanical vibrations incident on the diaphragm into electronic signals that can be readily amplified and transmitted to the earpiece worn by the operator. However, the human operator is still required to interpret the audio signals to deduce physiometric parameters such as heart rate and respiration rate.

In contrast, ultrasound imaging equipment has been developed to automate some of this data collection and interpretation. For example, ultrasound imagers can extract adult or fetal heart rate from recorded images or Doppler ultrasound. These imagers measure high frequency echoes that penetrate and reflect off of tissues within a body. A number of strategies have been developed to modulate the frequency of the sound to perform tomography using these ultrasound instruments. For example, high frequencies generate higher resolution images at shallower depths (e.g. subcutaneous tissue, lungs, vasculature) and lower frequencies generate lower resolution images at deeper depths (e.g. visceral organs). Ultrasound is used for a variety of diagnostic imaging purposes including examination and monitoring of infection, trauma, bowel obstruction, cardiac disorder, pregnancy staging, and fetal health. Though its versatility would make the ultrasound a particularly effective tool for use in point-of-care medicine, in the developing world, in wilderness expeditions, and in spaceflight, the typically high cost, power-requirements, and size of ultrasound equipment have prevented its adoption for many scenarios.

Furthermore, unlike stethoscopes, current ultrasound imagers require substantial training to use, yet still suffer from substantial inter-operator variability. These limitations have allowed ultrasound to augment, but not replace, stethoscopes.

SUMMARY

Owing to the complementary diagnostic information provided by stethoscopes and ultrasound systems, there is a need for systems and methods that utilize both of these technologies. Ideally, such systems and methods would also measure and incorporate information regarding physiological parameters, such as heart rate, blood pressure, body temperature, respiration rate, or $SpO_2$ (saturation of hemoglobin with $O_2$).

The systems and methods described herein generally relate to stethoscopes providing enhanced functionality over the stethoscopes that are commonly used by medical professionals. An enhanced stethoscope device and method for operating the enhanced stethoscope are provided. The enhanced stethoscope device generally operates by providing stethoscope sensors, ultrasonic sensors, and other sensors to obtain a series of measurements about a subject. The series of measurements may be correlated, such as by machine learning, to extract clinically relevant information. Also described are systems and methods for ultrasonic beamsteering by interference of an audio signal with an ultrasonic signal.

In a first broad aspect, a stethoscope device may comprise a stethoscope head. The audio head may comprise a mechanical diaphragm. The mechanical diaphragm may receive a stethoscopic audio signal from an object. The stethoscope device may further comprise a first ultrasonic transducer. The first ultrasonic transducer may transmit a first transmitted ultrasonic imaging signal to the object at a first frequency and receive a first received ultrasonic imaging signal from the object at the first frequency. The stethoscope device may further comprise a second ultrasonic transducer. The second ultrasonic transducer may transmit a second transmitted ultrasonic imaging signal to the object at a second frequency different from the first frequency and receive a second received ultrasonic imaging signal from the object at the second frequency. The first and second ultrasonic imaging transducers may transmit and receive simultaneously with one another.

The frequency of the first transmitted ultrasonic imaging signal may be selected from the group consisting of: 100 kHz, 200 kHz, 300 kHz, 400 kHz, 500 kHz, 650 kHz, 700 kHz, 800 kHz, 850 kHz, 900 kHz, 1 MHz, 2 MHz, 3 MHz, 5.5 MHz, 6 MHz, 8 MHz, and 11 MHz. The frequency of the second transmitted ultrasonic imaging signal may be in the frequency range of 0.5 Mhz-30 MHz. The frequency of the first received ultrasonic imaging signal may be selected from the group consisting of: 100 kHz, 200 kHz, 300 kHz, 400 kHz, 500 kHz, 650 kHz, 700 kHz, 800 kHz, 850 kHz, 900 kHz, 1 MHz, 2 MHz, 3 MHz, 5.5 MHz, 6 MHz, 8 MHz, and 11 MHz. The frequency of the second received ultrasonic imaging signal may be in the frequency range of 0.5 Mhz-30 MHz. The frequency of the first transmitted ultrasonic imaging signal may be in the frequency range of 0.5 MHz-30 MHz and the frequency of the second transmitted ultrasonic imaging signal may be in the frequency range of 0.5 MHz-30 MHz and may be distinct from the frequency of the first transmitted ultrasonic imaging signal. The frequency of the first received ultrasonic imaging signal may be in the frequency range of 0.5 MHz-30 MHz and the frequency of the second received ultrasonic imaging signal may be in the frequency range of 0.5 MHz-30 MHz and may be distinct from the frequency of the first received ultrasonic imaging signal.

The first received ultrasonic imaging signal may be normalized by the second received ultrasonic imaging signal.

The first ultrasonic transducer may comprise an element selected from the group consisting of: a lead zirconate titanate (PZT) element, a polyvinylidine fluoride (PVDF) element, a piezoelectric micromachined ultrasound transducer (PMUT) element, and a capacitive micromachined ultrasonic transducer (CMUT) element. The second ultrasonic transducer may comprise an element selected from the group consisting of: a PZT element, a PVDF element, a PMUT element, and a CMUT element.

The first ultrasonic transducer may have a bandwidth that partially overlaps with the bandwidth of at least one other ultrasonic imaging sensor.

The stethoscope device may comprise a housing coupled to one or more of the stethoscope head, the first ultrasonic transducer, and the second ultrasonic transducer. One or more of the stethoscope head, the first ultrasonic transducer, and the second ultrasonic transducer may be detachably coupled to the housing. One or more of the stethoscope head, the first ultrasonic transducer, and the second ultrasonic transducer may be physically coupled to the housing. One or more of the stethoscope head, the first ultrasonic transducer, and the second ultrasonic transducer may be functionally coupled to the housing.

The stethoscope device may further comprise a non-stethoscopic, non-ultrasonic sensor for detecting a non-stethoscopic, non-ultrasonic signal. The non-stethoscopic, non-ultrasonic sensor may be selected from the group consisting of: a non-stethoscopic audio sensor, a temperature sensor, an optical sensor, an electrical sensor, and an electrochemical sensor. The non-stethoscopic, non-ultrasonic sensor may be configured to detect a signal originating from the group consisting of: a body temperature, a respiration rate, a respiration quality, a respiration pathology, a blood pressure level, a blood glucose concentration level, a blood gas concentration level, and a blood oxygenation saturation ($spO_2$) level.

The stethoscope head may be functionally coupled to the first and second ultrasonic transducers.

The stethoscope device may comprise a battery. The stethoscope device may comprise a power connector for receiving electrical power. The stethoscope device may comprise an inductive power coil for receiving electrical power. The stethoscope device may comprise an inductive power coil for transmitting and receiving data.

The stethoscope device may comprise a control for operating the device in one or more of a stethoscopic mode, an ultrasonic imaging mode, or a non-stethoscopic, non-ultrasonic mode. The control may comprise a user interface. The user interface may be configured to provide a user with feedback based on the stethoscopic signal, the ultrasonic signal, or the non-stethoscopic, non-ultrasonic signal. The user interface may comprise a touchscreen device.

The stethoscope device may comprise a wireless networking modality. The wireless networking modality may be configured to communicate the stethoscopic audio signal, received ultrasonic signal, or non-stethoscopic, non-ultrasonic signal to a peripheral device.

The stethoscope device may comprise a microphone and speaker. The microphone and speaker may enable communication between an operator of the enhanced stethoscope device and the enhanced stethoscope device.

In a second broad aspect, a stethoscope device may comprise a stethoscope head. The stethoscope head may comprise a mechanical diaphragm. The mechanical diaphragm may receive a stethoscopic audio signal from an object. The stethoscope device may further comprise an ultrasonic transducer. The ultrasonic transducer may transmit a transmitted ultrasonic imaging signal to the object and receive a received ultrasonic imaging signal from the object. The stethoscope device may further comprise a non-stethoscopic, non-ultrasonic sensor. The non-stethoscopic, non-ultrasonic sensor may detect a non-stethoscopic, non-ultrasonic signal from the object.

The stethoscope device may comprise a housing coupled to the stethoscope head, the ultrasonic transducer, and the non-stethoscopic, non-ultrasonic sensor. One or more of the stethoscope head, the ultrasonic transducer, and the non-stethoscopic, non-ultrasonic sensor may be detachably coupled to the housing. One or more of the stethoscope head, the ultrasonic transducer, and the non-stethoscopic, non-ultrasonic sensor may be physically coupled to the housing. One or more of the stethoscope head, the ultrasonic transducer, and the non-stethoscopic, non-ultrasonic sensor may be functionally coupled to the housing.

The received ultrasonic imaging signal received from the object may be a scattered signal of the transmitted ultrasonic imaging signal.

The non-stethoscopic, non-ultrasonic sensor may be selected from the group consisting of: a non-stethoscopic audio sensor, a temperature sensor, an optical sensor, an electrical sensor, a chemical sensor, and an electrochemical sensor. The non-stethoscopic, non-ultrasonic sensor may be configured to detect a signal corresponding with one or more of: a body temperature, a respiration rate, a respiration volume, a respiration quality, a respiratory pathology, a blood pressure level, a blood glucose concentration, a blood gas concentration level, and a blood oxygenation saturation ($spO_2$) level.

The ultrasonic transducer may be attached to the stethoscope head.

The stethoscope device may comprise a rechargeable or non-rechargeable battery. The stethoscope device may comprise a power connector for receiving electrical power. The stethoscope device may comprise an inductive power coil for receiving electrical power. The stethoscope device may comprise an inductive power coil for transmitting and receiving data.

The stethoscope device may comprise a control for operating the device in one or more of a stethoscopic mode, an ultrasonic imaging mode, a non-stethoscopic, non-ultrasonic mode. The control may comprise a user interface. The user interface may be configured to provide a user with feedback based on the stethoscopic signal, ultrasonic signal, or non-stethoscopic, non-ultrasonic signal. The user interface may comprise a display. The display may display a 2-dimensional representation of a sample being imaged. The user interface may comprise a touchscreen device.

The stethoscope device may comprise a wireless networking modality. The wireless networking modality may be configured to communicate the stethoscopic audio signal, received ultrasonic signal, or non-stethoscopic, non-ultrasonic signal to a peripheral device.

The stethoscope device may comprise a microphone and speaker. The microphone and speaker may enable communication between an operator of the enhanced stethoscope device and the enhanced stethoscope device.

In a third broad aspect, a stethoscope device may comprise a stethoscope head. The stethoscope head may comprise a mechanical diaphragm. The mechanical diaphragm may receive a stethoscopic audio signal from an object. The stethoscope device may further comprise an ultrasonic transducer. The ultrasonic transducer may transmit a transmitted ultrasonic imaging signal to the object and receive a received ultrasonic imaging signal from the object. The stethoscope device may further comprise a model. The model may correlate the stethoscopic audio signal and the received ultrasonic imaging signal.

The stethoscope device may comprise a housing coupled to the stethoscope head and ultrasonic transducer. One or both of the stethoscope head and the ultrasonic transducer may be detachably coupled to the housing. One or both of the stethoscope head and the ultrasonic transducer may be physically coupled to the housing. One or both of the stethoscope head and ultrasonic transducer may be functionally coupled to the housing.

The stethoscope device may comprise a non-stethoscopic, non-ultrasonic sensor for detecting a non-stethoscopic, non-ultrasonic signal. The non-stethoscopic, non-ultrasonic sensor may be selected from the group consisting of: a non-stethoscopic audio sensor, a temperature sensor, an optical sensor, an electrical sensor, a chemical sensor and an electrochemical sensor. The non-stethoscopic, non-ultrasonic sensor may be configured to detect a signal corresponding with from one or more of: a body temperature, a respiration rate, a blood pressure level, and a blood oxygenation saturation ($spO_2$) level.

The model may correlate a first signal selected from the group consisting of: (a) a stethoscopic audio signal, (b) an ultrasonic imaging signal, and (c) a non-ultrasonic signal; with a second signal selected from the group consisting of: (x) a stethoscopic audio signal, (y) an ultrasonic imaging signal, and (z) a non-ultrasonic signal; thereby generating an extracted feature parameter.

The model may correlate the first and second signals by: convolving the first signal with a first weighting function to form a first weighted signal; convolving the second signal with a second weighting function to form a second weighted signal; and performing auto-correlation or cross-correlation on the first and second weighted signals to generate the extracted feature parameter.

The model may correlate the first and second signals by: transforming the first and second signals, respectively, with one or more of (i) a Fourier transform, (ii) a Z-transform, (iii) a wavelet transform, (iv) a cosine series, (v) a sine series, or (vi) a Taylor series; to form first and second transformed signals, respectively; and cross-correlating or auto-correlating the first and second transformed signals to generate a feature parameter.

The model may correlate the first and second signals by: encoding the first and second signals; and mapping the first and second signals to a set of features using a machine learning technique. The machine learning technique may be selected from the group consisting of: a Diabolo network, a neural network, and a sparse dictionary.

The ultrasonic transducer may be attached to the head of the stethoscope.

The stethoscope device may comprise a rechargeable or non-rechargeable battery. The stethoscope device may comprise a power connector for receiving electrical power. The stethoscope device may comprise an inductive power coil for receiving electrical power. The stethoscope device may comprise an inductive power coil for transmitting and receiving data.

The stethoscope device may comprise a control for operating the device in one or more of a stethoscopic mode, an ultrasonic imaging mode, or a non-stethoscopic, non-ultrasonic mode. The control may comprise a user interface. The user interface may be configured to provide a user with feedback based on one or more of the stethoscopic signal, the ultrasonic signal, or the non-stethoscopic, non-ultrasonic signal. The user interface may comprise a touchscreen device.

The stethoscope device may comprise a wireless networking modality. The wireless networking modality may be configured to communicate one or more of the stethoscopic audio signal, the received ultrasonic signal, or the non-stethoscopic, non-ultrasonic signal to a peripheral device.

The stethoscope device may comprise a microphone and speaker. The microphone and speaker may enable communication between an operator of the enhanced stethoscope device and the enhanced stethoscope device.

In a fourth broad aspect, a stethoscope device may comprise a stethoscope head. The stethoscope head may comprise a mechanical diaphragm. The mechanical diaphragm may receive a stethoscopic audio signal from an object. The stethoscope device may further comprise an ultrasonic transducer. The ultrasonic transducer may transmit a transmitted ultrasonic imaging signal to the object and receive a received ultrasonic imaging signal from the object. The stethoscope device may further comprise an audio transducer. The audio transducer may transmit an audio signal to the object. The stethoscope device may further comprise an interference circuit. The interference circuit may interfere the transmitted ultrasonic imaging signal with the audio signal to steer the ultrasonic imaging signal to the object.

The stethoscope device may comprise a housing coupled to one or more of the stethoscope head, the ultrasonic transducer, the audio transducer, and the interference circuit. One or more of the stethoscope head, the ultrasonic transducer, the audio transducer, and the interference circuit may be detachably coupled to the housing. One or more of the stethoscope head, the ultrasonic transducer, the audio transducer, and the interference circuit may be physically coupled to the housing. One or more of the stethoscope head, the ultrasonic transducer, the audio transducer, and the interference circuit may be functionally coupled to the housing.

The interference circuit may interfere the transmitted ultrasonic imaging signal with the audio signal based on a model of the object response to the audio signal. The model may correlate the ultrasonic imaging signal with the audio signal and generate an extracted feature parameter.

The model may correlate the ultrasonic imaging signal and the audio signal by: convolving the ultrasonic imaging signal with a first weighting function to form a weighted ultrasonic imaging signal; convolving the audio signal with a second weighting function to form a weighted audio signal; and performing auto-correlation or cross-correlation on the weighted ultrasonic imaging signal and the weight audio signal to generate a feature parameter.

The model may correlate the ultrasonic imaging signal and the audio signal by: transforming the ultrasonic imaging and audio signals, respectively, with one or more of (i) a Fourier transform, (ii) a Z-transform, (iii) a wavelet transform, (iv) a cosine series, (v) a sine series, or (vi) a Taylor series; to form transformed ultrasonic imaging and transformed audio signals, respectively; and cross-correlating or auto-correlating the transformed ultrasonic imaging signal and the transformed audio signal to generate a feature parameter.

The model may correlate the ultrasonic imaging signal and the audio signal by: encoding the ultrasonic imaging signal and the audio signal; and mapping the ultrasonic imaging signal and the audio signal to a set of features using a machine learning technique. The machine learning technique may be selected from the group consisting of: a Diabolo network, a neural network, and a sparse dictionary.

The stethoscope device may comprise a non-stethoscopic, non-ultrasonic sensor for detecting a non-stethoscopic, non-ultrasonic signal. The non-stethoscopic, non-ultrasonic sensor may be selected from the group consisting of: a non-stethoscopic audio sensor, a temperature sensor, an optical sensor, an electrical sensor, a chemical sensor, and an electrochemical sensor. The non-stethoscopic, non-ultrasonic sensor may be configured to detect a signal corresponding with the group consisting of: a body temperature, a respiration rate, a respiration quality, a respiration pathology, a blood pressure level, a blood glucose concentration level, a blood gas concentration level, and a blood oxygenation saturation ($spO_2$) level.

The ultrasonic transducer may be detachably or non-detachably attached to the head of the stethoscope. The ultrasonic transducer may be attached to an acoustic matching layer. The ultrasonic transducer may be detachably or non-detachably attached to the head of the stethoscope.

The stethoscope device may comprise a rechargeable or non-rechargeable battery. The stethoscope device may comprise a power connector for receiving electrical power. The stethoscope device may comprise an inductive power coil for receiving electrical power. The stethoscope device may comprise an inductive power coil for transmitting and receiving data.

The stethoscope device may comprise a control for operating the device in one or more of a stethoscopic mode, an ultrasonic imaging mode, and a non-stethoscopic, non-ultrasonic mode. The control may comprise a user interface. The user interface may be configured to provide a user with feedback based on one or more of the stethoscopic signal, the ultrasonic signal, and the non-stethoscopic, non-ultrasonic signal. The user interface may comprise a touchscreen device.

The stethoscope device may comprise a wireless networking modality. The wireless networking modality may be configured to communicate one or more of the stethoscopic audio signal, the received ultrasonic signal, and the non-stethoscopic, non-ultrasonic signal to a peripheral device.

The stethoscope device may comprise a microphone and speaker. The microphone and speaker may enable communication between an operator of the enhanced stethoscope device and the enhanced stethoscope device.

In a fifth broad aspect, a method may comprise receiving a stethoscopic audio signal from an object. The stethoscopic audio signal may be received by a stethoscope head comprising a mechanical diaphragm. The method may further comprise transmitting a first transmitted ultrasonic imaging signal to the object at a first frequency and receiving a first received ultrasonic imaging signal from the object at the first frequency. The first ultrasonic imaging signal may be transmitted and received by a first ultrasonic transducer. The method may further comprise transmitting a second transmitted ultrasonic imaging signal to the object at a second frequency different from the first frequency and receiving a second received ultrasonic imaging signal from the object at the second frequency. The second ultrasonic imaging signal may be transmitted and received by a second ultrasonic transducer. The first and second ultrasonic transducers may transmit and receive simultaneously with one another.

The frequency of the first transmitted ultrasonic imaging signal may be selected from the group consisting of: 100 kHz, 200 kHz, 300 kHz, 400 kHz, 500 kHz, 650 kHz, 700 kHz, 800 kHz, 850 kHz, 900 k Hz, 1 MHz, 2 MHz, 3 MHz, 5.5 MHz, 6 MHz, 8 MHz, and 11 MHz; and the frequency of the second transmitted ultrasonic imaging signal may be in the frequency range of 0.5 Mhz-30 MHz. The frequency of the first transmitted ultrasonic imaging signal may be selected from the group consisting of: 100 kHz, 200 kHz, 300 kHz, 400 kHz, 500 kHz, 650 kHz, 700 kHz, 800 kHz, 850 kHz, 900 kHz, 1 MHz, 2 MHz, 3 MHz, 5.5 MHz, 6 MHz, 8 MHz, and 11 MHz; and the frequency of the second transmitted ultrasonic imaging signal may be in the frequency range of 0.5 Mhz-30 MHz. The frequency of the first received ultrasonic imaging signal may be selected from the group consisting of: 100 kHz, 200 kHz, 300 kHz, 400 kHz, 500 kHz, 650 kHz, 700 kHz, 800 kHz, 850 kHz, 900 kHz, 1 MHz, 2 MHz, 3 MHz, 5.5 MHz, 6 MHz, 8 MHz, and 11 MHz; and the frequency of the second received ultrasonic imaging signal may be in the frequency range of 0.5 Mhz-30 MHz. The frequency of the first transmitted ultrasonic imaging signal may be in the frequency range of 0.5 MHz-30 MHz and the frequency of the second transmitted ultrasonic imaging signal may be in the frequency range of 0.5 MHz-30 MHz and is distinct from the frequency of the first transmitted ultrasonic imaging signal. The frequency of the first received ultrasonic imaging signal may be in the frequency range of 0.5 MHz-30 MHz and the frequency of the second received ultrasonic imaging signal may be in the frequency range of 0.5 MHz-30 MHz and is distinct from the frequency of the first received ultrasonic imaging signal.

The first received ultrasonic imaging signal may be normalized by the second received ultrasonic imaging signal.

The first ultrasonic transducer may comprise an element selected from the group consisting of: a lead zirconate titanate (PZT) element, a polyvinylidine fluoride (PVDF) element, a piezoelectric micromachined ultrasound transducer (PMUT) element, and a capacitive micromachined ultrasonic transducer (CMUT) element; and the second ultrasonic transducer may comprise an element selected from the group consisting of: a PZT element, a PVDF element, a PMUT element, and a CMUT element.

The first ultrasonic transducer may have a bandwidth that partially overlaps with the bandwidth of at least one other ultrasonic imaging sensor.

The method may further comprise coupling a housing to one or more of the stethoscope head, the first ultrasonic transducer, and the second ultrasonic transducer. One or more of the stethoscope head, the first ultrasonic transducer, and the second ultrasonic transducer may be detachably coupled to the housing. One or more of the stethoscope head, the first ultrasonic transducer, and the second ultrasonic transducer may be physically coupled to the housing. One or more of the stethoscope head, the first ultrasonic transducer, and the second ultrasonic transducer may functionally coupled to the housing.

The method may further comprise detecting a non-stethoscopic, non-ultrasonic signal. The non-stethoscopic, non-ultrasonic signal may be detected by a non-stethoscopic, non-ultrasonic sensor. The non-stethoscopic, non-ultrasonic sensor may be selected from the group consisting of: a non-stethoscopic audio sensor, a temperature sensor, an optical sensor, an electrical sensor, and an electrochemical sensor. The non-stethoscopic, non-ultrasonic sensor may be configured to detect a signal originating from the group consisting of: a body temperature, a respiration rate, a respiration quality, a respiration pathology, a blood pressure level, a blood glucose concentration level, a blood gas concentration level, and a blood oxygenation saturation ($spO_2$) level.

The stethoscope head may be functionally coupled to the first and second ultrasonic transducers.

The method may further comprise providing power to the stethoscope head, first ultrasonic imaging transducer, and second ultrasonic imaging transducer. The power may be provided by a battery. The power may be provided by a power connector for receiving electrical power. The power may be provided by an inductive power coil for receiving electrical power.

The method may further comprise transmitting and receiving data. Transmitting and receiving data may be performed by an inductive power coil for transmitting and receiving data.

The method may further comprise operating the device in one or more of a stethoscopic mode, an ultrasonic imaging mode, or a non-stethoscopic, non-ultrasonic mode. Operation of the device may be performed by a control. The control may comprise a user interface. The user interface may be configured to provide a user with feedback based on the stethoscopic signal, the ultrasonic signal, or the non-stethoscopic, non-ultrasonic signal. The user interface may comprise a touchscreen device.

The method may further comprise communicating the stethoscopic audio signal, received ultrasonic signal, or non-stethoscopic, non-ultrasonic signal to a peripheral device. The communication may be by a wireless networking modality.

The method may further comprise enabling communication between an operator of the stethoscope device and the stethoscope device. The communication may be enabled by a microphone and speaker.

In a sixth broad aspect, a method may comprise receiving a stethoscopic audio signal from an object. The stethoscopic audio signal may be received by a stethoscope comprising a mechanical diaphragm. The method may further comprise transmitting a transmitted ultrasonic imaging signal to the object and receiving a received ultrasonic imaging signal from the object. The ultrasonic imaging signal may be transmitted and received by an ultrasonic transducer. The method may further comprise detecting a non-stethoscopic, non-ultrasonic signal from the object. The non-stethoscopic, non-ultrasonic signal may be detected by a non-stethoscopic, non-ultrasonic sensor.

The method may further comprise coupling a housing to the stethoscope head, the ultrasonic transducer, and the non-stethoscopic, non-ultrasonic sensor. One or more of the stethoscope head, the ultrasonic transducer, and the non-stethoscopic, non-ultrasonic sensor may be detachably coupled to the housing. One or more of the stethoscope head, the ultrasonic transducer, and the non-stethoscopic, non-ultrasonic sensor may be physically coupled to the housing. One or more of the stethoscope head, the ultrasonic transducer, and the non-stethoscopic, non-ultrasonic sensor may be functionally coupled to the housing.

The received ultrasonic imaging signal received from the object may be a scattered signal of the transmitted ultrasonic imaging signal.

The non-stethoscopic, non-ultrasonic sensor may be selected from the group consisting of: a non-stethoscopic audio sensor, a temperature sensor, an optical sensor, an electrical sensor, a chemical sensor, and an electrochemical sensor. The non-stethoscopic, non-ultrasonic sensor may be configured to detect a signal corresponding with one or more of: a body temperature, a respiration rate, a respiration volume, a respiration quality, a respiratory pathology, a blood pressure level, a blood glucose concentration, a blood gas concentration level, and a blood oxygenation saturation ($spO_2$) level.

The ultrasonic transducer may be attached to the stethoscope head.

The method may further comprise providing power to the stethoscope head, first ultrasonic imaging transducer, and second ultrasonic imaging transducer. The power may be provided by a battery. The power may be provided by a power connector for receiving electrical power. The power may be provided by an inductive power coil for receiving electrical power.

The method may further comprise transmitting and receiving data. Transmitting and receiving data may be performed by an inductive power coil for transmitting and receiving data.

The method may further comprise operating the device in one or more of a stethoscopic mode, an ultrasonic imaging mode, or a non-stethoscopic, non-ultrasonic mode. Operation of the device may be performed by a control. The control may comprise a user interface. The user interface may be configured to provide a user with feedback based on the stethoscopic signal, the ultrasonic signal, or the non-stethoscopic, non-ultrasonic signal. The user interface may comprise a touchscreen device.

The method may further comprise communicating the stethoscopic audio signal, received ultrasonic signal, or non-stethoscopic, non-ultrasonic signal to a peripheral device. The communication may be by a wireless networking modality.

The method may further comprise enabling communication between an operator of the stethoscope device and the stethoscope device. The communication may be enabled by a microphone and speaker.

In a seventh broad aspect, a method may comprise receiving a stethoscopic audio signal from an object. The stethoscopic audio signal may be received by a stethoscope comprising a mechanical diaphragm. The method may further comprise transmitting a transmitted ultrasonic imaging signal to the object and receiving a received ultrasonic imaging signal from the object. The ultrasonic imaging signal may be transmitted and received by an ultrasonic transducer. The method may further comprise correlating the stethoscopic audio signal and the received ultrasonic imaging signal. The stethoscopic audio signal and received ultrasonic imaging signal may be correlated by a model.

The method may further comprise coupling a housing to the stethoscope head and ultrasonic transducer. One or both of the stethoscope head and the ultrasonic transducer may be detachably coupled to the housing. One or both of the stethoscope head and the ultrasonic transducer may be physically coupled to the housing. One or both of the stethoscope head and ultrasonic transducer may be functionally coupled to the housing.

The method may further comprise detecting a non-stethoscopic, non-ultrasonic signal. The non-stethoscopic, non-ultrasonic signal may be detected by a non-stethoscopic, non-ultrasonic sensor. The non-stethoscopic, non-ultrasonic sensor may be selected from the group consisting of: a non-stethoscopic audio sensor, a temperature sensor, an optical sensor, an electrical sensor, a chemical sensor and an electrochemical sensor. The non-stethoscopic, non-ultrasonic sensor may be configured to detect a signal corresponding with from one or more of: a body temperature, a respiration rate, a blood pressure level, and a blood oxygenation saturation ($spO_2$) level.

The model may correlate a first signal selected from the group consisting of: (a) a stethoscopic audio signal, (b) an ultrasonic imaging signal, and (c) a non-ultrasonic signal; with a second signal selected from the group consisting of: (x) a stethoscopic audio signal, (y) an ultrasonic imaging signal, and (z) a non-ultrasonic signal; thereby generating an extracted feature parameter.

The model may correlate the first and second signals by: convolving the first signal with a first weighting function to form a first weighted signal; convolving the second signal with a second weighting function to form a second weighted signal; and performing auto-correlation or cross-correlation on the first and second weighted signals to generate the extracted feature parameter.

The model may correlate the first and second signals by: transforming the first and second signals, respectively, with one or more of (i) a Fourier transform, (ii) a Z-transform, (iii) a wavelet transform, (iv) a cosine series, (v) a sine series, or (vi) a Taylor series; to form first and second transformed signals, respectively; and cross-correlating or auto-correlating the first and second transformed signals to generate a feature parameter.

The model may correlate the first and second signals by: encoding the first and second signals; and mapping the first and second signals to a set of features using a machine learning technique. The machine learning technique may be selected from the group consisting of: a Diabolo network, a neural network, and a sparse dictionary.

The ultrasonic transducer may be attached to the head of the stethoscope.

The method may further comprise providing power to the stethoscope head, first ultrasonic imaging transducer, and second ultrasonic imaging transducer. The power may be provided by a battery. The power may be provided by a power connector for receiving electrical power. The power may be provided by an inductive power coil for receiving electrical power.

The method may further comprise transmitting and receiving data. Transmitting and receiving data may be performed by an inductive power coil for transmitting and receiving data.

The method may further comprise operating the device in one or more of a stethoscopic mode, an ultrasonic imaging mode, or a non-stethoscopic, non-ultrasonic mode. Operation of the device may be performed by a control. The control may comprise a user interface. The user interface may be configured to provide a user with feedback based on the stethoscopic signal, the ultrasonic signal, or the non-stethoscopic, non-ultrasonic signal. The user interface may comprise a touchscreen device.

The method may further comprise communicating the stethoscopic audio signal, received ultrasonic signal, or non-stethoscopic, non-ultrasonic signal to a peripheral device. The communication may be by a wireless networking modality.

The method may further comprise enabling communication between an operator of the stethoscope device and the stethoscope device. The communication may be enabled by a microphone and speaker.

In an eighth broad aspect, a method may comprise receiving a stethoscopic audio signal from an object. The stethoscopic audio signal may be received by a stethoscope comprising a mechanical diaphragm. The method may further comprise transmitting a transmitted ultrasonic imaging signal to the object and receiving a received ultrasonic imaging signal from the object. The ultrasonic imaging signal may be transmitted and received by an ultrasonic transducer. The method may further comprise transmitting an audio signal to the object. The audio signal may be transmitted by an audio transducer. The method may further comprise interfering the transmitted ultrasonic imaging signal with the audio signal to steer the ultrasonic imaging signal to the object. The transmitted ultrasonic imaging signal may be interfered with the audio signal by an interference circuit.

The method may further comprise coupling a housing to one or more of the stethoscope head, the ultrasonic transducer, the audio transducer, and the interference circuit. One or more of the stethoscope head, the ultrasonic transducer, the audio transducer, and the interference circuit may be detachably coupled to the housing. One or more of the stethoscope head, the ultrasonic transducer, the audio transducer, and the interference circuit may be physically coupled to the housing. One or more of the stethoscope head, the ultrasonic transducer, the audio transducer, and the interference circuit may be functionally coupled to the housing.

The interference circuit may interfere the transmitted ultrasonic imaging signal with the audio signal based on a model of the object response to the audio signal. The model may correlate the ultrasonic imaging signal with the audio signal and generates an extracted feature parameter.

The model may correlate the ultrasonic imaging signal and the audio signal by: convolving the ultrasonic imaging signal with a first weighting function to form a weighted ultrasonic imaging signal; convolving the audio signal with a second weighting function to form a weighted audio signal; and performing auto-correlation or cross-correlation on the weighted ultrasonic imaging signal and the weight audio signal to generate a feature parameter.

The model may correlate the ultrasonic imaging signal and the audio signal by: transforming the ultrasonic imaging and audio signals, respectively, with one or more of (i) a Fourier transform, (ii) a Z-transform, (iii) a wavelet transform, (iv) a cosine series, (v) a sine series, or (vi) a Taylor series; to form transformed ultrasonic imaging and transformed audio signals, respectively; and cross-correlating or auto-correlating the transformed ultrasonic imaging signal and the transformed audio signal to generate a feature parameter. The model may correlate the ultrasonic imaging signal and the audio signal by: encoding the ultrasonic imaging signal and the audio signal; and mapping the ultrasonic imaging signal and the audio signal to a set of features using a machine learning technique. The machine learning technique may be selected from the group consisting of: a Diabolo network, a neural network, and a sparse dictionary.

The method may further comprise detecting a non-stethoscopic, non-ultrasonic signal. The non-stethoscopic, non-ultrasonic signal may be detected by a non-stethoscopic, non-ultrasonic sensor. The non-stethoscopic, non-ultrasonic sensor may be selected from the group consisting of: a non-stethoscopic audio sensor, a temperature sensor, an optical sensor, an electrical sensor, a chemical sensor, and an electrochemical sensor. The non-stethoscopic, non-ultrasonic sensor may be configured to detect a signal corresponding with the group consisting of: a body temperature, a respiration rate, a respiration quality, a respiration pathology, a blood pressure level, a blood glucose concentration level, a blood gas concentration level, and a blood oxygenation saturation ($spO_2$) level.

The ultrasonic transducer may be detachably or non-detachably attached to the head of the stethoscope. The ultrasonic transducer may be attached to an acoustic matching layer.

The method may further comprise providing power to the stethoscope head, first ultrasonic imaging transducer, and second ultrasonic imaging transducer. The power may be provided by a battery. The power may be provided by a power connector for receiving electrical power. The power may be provided by an inductive power coil for receiving electrical power.

The method may further comprise transmitting and receiving data. Transmitting and receiving data may be performed by an inductive power coil for transmitting and receiving data.

The method may further comprise operating the device in one or more of a stethoscopic mode, an ultrasonic imaging mode, or a non-stethoscopic, non-ultrasonic mode. Operation of the device may be performed by a control. The control may comprise a user interface. The user interface may be configured to provide a user with feedback based on the stethoscopic signal, the ultrasonic signal, or the non-stethoscopic, non-ultrasonic signal. The user interface may comprise a touchscreen device.

The method may further comprise communicating the stethoscopic audio signal, received ultrasonic signal, or non-stethoscopic, non-ultrasonic signal to a peripheral device. The communication may be by a wireless networking modality.

The method may further comprise enabling communication between an operator of the stethoscope device and the stethoscope device. The communication may be enabled by a microphone and speaker.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2A schematically illustrates a stethoscope head comprising a mechanical diaphragm and a plurality of ultrasonic transducers.

FIG. 2B schematically illustrates simultaneous actuation of the plurality of ultrasonic transducers.

FIG. 5A schematically illustrates a side view of a stethoscope head comprising a mechanical diaphragm, a plurality of ultrasound transducers, and a plurality of non-stethoscopic, non-ultrasonic sensors.

FIG. 5B schematically illustrates a perspective view of a stethoscope head comprising a mechanical diaphragm, a plurality of ultrasound transducers, and a plurality of non-stethoscopic, non-ultrasonic sensors.

DETAILED DESCRIPTION

While various embodiments of the invention are shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used herein, like characters refer to like elements.

The term "subject," as used herein, generally refers to an animal, such as a mammalian species (e.g., human) or avian (e.g., bird) species, or other organism, such as a plant. The subject can be a vertebrate, a mammal, a mouse, a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, or an individual that is in need of therapy or suspected of needing therapy. A subject can be a patient.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Figure 1:
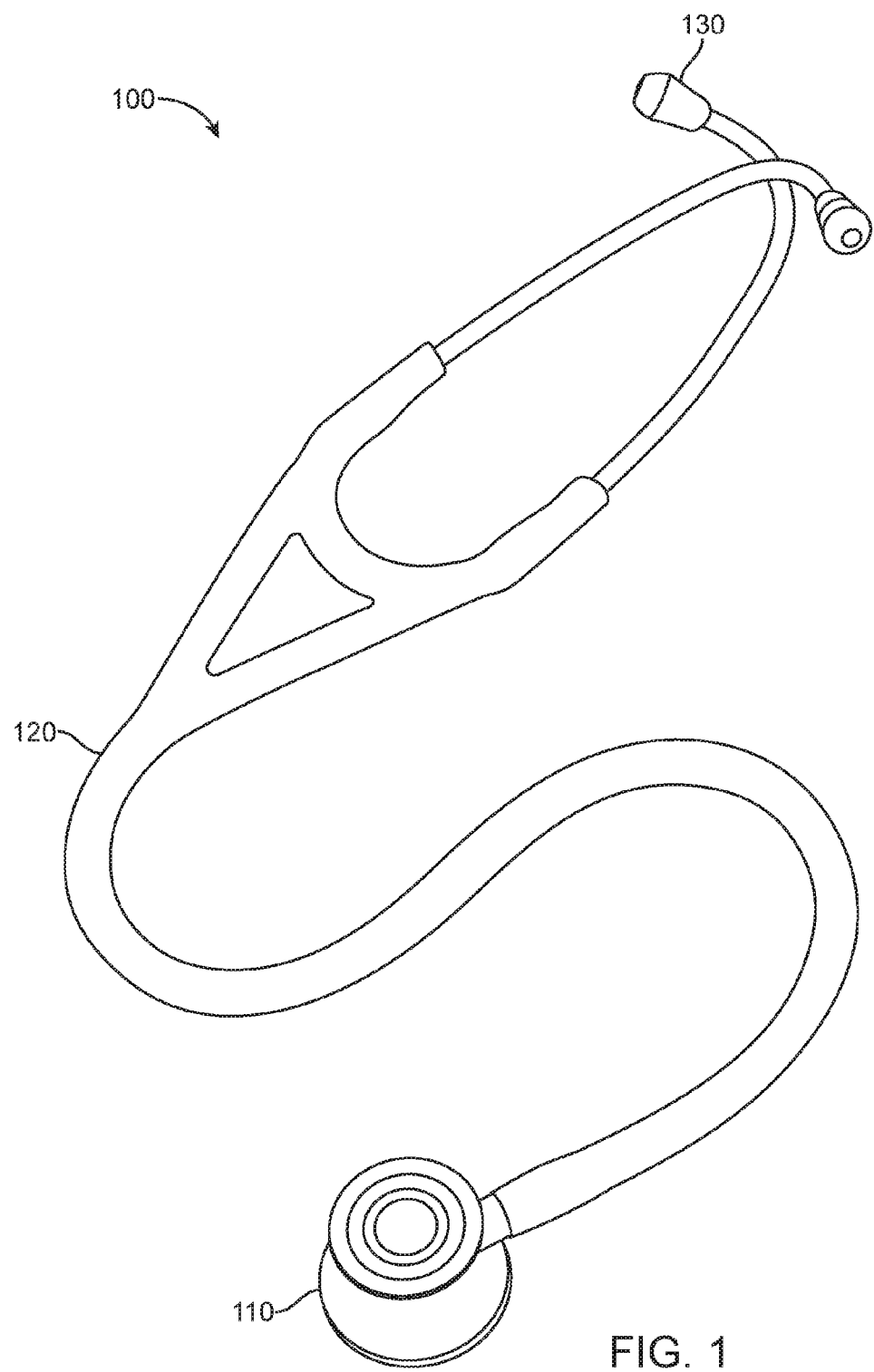
FIG. 1 schematically illustrates a stethoscope device comprising a stethoscope head.

FIG. 1 schematically illustrates a stethoscope device comprising a stethoscope head. The stethoscope device 100 may comprise a head 110, tubing 120, and one or two ear pieces 130. The head may comprise a mechanical diaphragm, as described herein. The mechanical diaphragm may be configured to mechanically amplify audio signals. For instance, the mechanical diaphragm may amplify audio signals that have a frequency within a range from about 0.01 Hz to about 3 kHz. The head may be placed in contact with or in proximity to a sample to be examined, such as a patient's chest, stomach, limb such as an arm or leg, or any other body part of the patient. The mechanical diaphragm may amplify audio signals associated with one or more biological processes occurring within the patient. For instance, the mechanical diaphragm may amplify audio signals associated with a patient's heartbeat, breathing, blood flow, digestion, or any other biological process that produces audio signals. The head may further comprise one or more non-stethoscopic audio sensors, as described herein.

The tubing may direct audio signals that are amplified by the mechanical diaphragm of the head to the one or two ear pieces. The tubing may comprise hollow tubing. The hollow tubing may be filled with air. The tubing may be flexible.

The one or two ear pieces may be worn within one or two ears of a user of the stethoscope device. A user may be a doctor, nurse, emergency medical technician, field medic, or any other medical professional. In some cases, a user may be a person without formal medical training, such as a friend or relative of a patient or a patient himself or herself. The one or two ear pieces may direct amplified audio signals from the mechanical diaphragm to one or two ears of the user. In this manner, the user may listen directly to the audio signals captured and amplified by the mechanical diaphragm.

FIG. 2A schematically illustrates a stethoscope head 110 comprising a mechanical diaphragm 200 and a plurality of ultrasonic transducers 210A-D. The mechanical diaphragm may be implemented on a surface of the stethoscope head or within the stethoscope head. The plurality of ultrasonic transducers may be implemented on a surface of the stethoscope head or within the stethoscope head. Though depicted as four ultrasonic transducers in FIG. 2A, the plurality of ultrasonic transducers may comprise 2, 3, 4, 5, 6, 7, 8, 9, 10, 11, 12, 13, 14, 15, 16, or more than 16 ultrasonic transducers. Each ultrasonic transducer of the plurality of ultrasonic transducers may be a lead zirconate titante (PZT) transducer, a polyvinylidine fluoride (PVD) transducer, a piezoelectric micromachine ultrasound transducer (PMUT), or a capacitive micromachine ultrasonic transducer (PMUT), or any other ultrasonic transducer. Each ultrasonic transducer of the plurality may be of the same type. One or more ultrasonic transducer of the plurality may be of a different type than other ultrasonic transducer of the plurality.

The stethoscope device may further comprise a housing (not shown in FIG. 1 or FIG. 2A). The housing may be coupled to one or more of the stethoscope head, the first ultrasonic transducer, and the second ultrasonic transducer. The housing may be detachably coupled to one or more of the stethoscope head, the first ultrasonic transducer, and the second ultrasonic transducer. The housing may be physically coupled to one or more of the stethoscope head, the first ultrasonic transducer, and the second ultrasonic transducer. The housing may be functionally coupled to one or more of the stethoscope head, the first ultrasonic transducer, and the second ultrasonic transducer.

Each ultrasonic transducer of the plurality of ultrasonic transducers may be configured to transmit a transmitted ultrasonic imaging signal to an object. Each ultrasonic transducer of the plurality may be configured to transmit a transmitted ultrasonic imaging signal having a frequency of about 100 kHz, about 200 kHz, about 300 kHz, about 400 kHz, about 500 kHz, about 650 kHz, about 700 kHz, about 800 kHz, about 850 kHz, about 900 kHz, about 1 MHz, about 2 MHz, about 3 MHz, about 5.5 MHz, about 6 MHz, about 8 MHz, about 11 MHz, about 15 MHz, about 20 MHz, about 25 MHz, or about 30 MHz. Each ultrasonic transducer of the plurality may be configured to transmit a transmitted ultrasonic imaging signal having a frequency that is within a range defined by any two of the preceding values.

Each ultrasonic transducer of the plurality of ultrasonic transducers may be configured to receive a received ultrasonic imaging signal from an object. Each ultrasonic transducer of the plurality may be configured to receive a received ultrasonic imaging signal having a frequency of about 100 kHz, about 200 kHz, about 300 kHz, about 400 kHz, about 500 kHz, about 650 kHz, about 700 kHz, about 800 kHz, about 850 kHz, about 900 kHz, about 1 MHz, about 2 MHz, about 3 MHz, about 5.5 MHz, about 6 MHz, about 8 MHz, about 11 MHz, about 15 MHz, about 20 MHz, about 25 MHz, or about 30 MHz. Each ultrasonic transducer of the plurality may be configured to receive a received ultrasonic imaging signal having a frequency that is within a range defined by any two of the preceding values.

Each ultrasonic transducer of the plurality may be configured both to transmit and to receive. Each ultrasonic transducer of the plurality may be configured to transmit transmitted ultrasonic imaging signals or receive received ultrasonic imaging signals at a frequency that is the same as one or more of the frequencies transmitted or received by other ultrasonic transducer of the plurality. Each ultrasonic transducer of the plurality may be configured to transmit transmitted ultrasonic imaging signals or receive received ultrasonic imaging signals at a frequency that is different from all of frequencies transmitted or received by all other ultrasonic transducer of the plurality. Each of the ultrasonic transducer of the plurality may be configured to transmit or receive at the same time as one or more other ultrasonic transducer of the plurality.

For instance, a first transmitted imaging signal of a first ultrasonic transducer of the plurality may have a frequency of about 100 kHz, about 200 kHz, about 300 kHz, about 400 kHz, about 500 kHz, about 650 kHz, about 700 kHz, about 800 kHz, about 850 kHz, about 900 kHz, about 1 MHz, about 2 MHz, about 3 MHz, about 5.5 MHz, about 6 MHz, about 8 MHz, or about 11 MHz. A second transmitted imaging signal of a second ultrasonic transducer of the plurality may have a frequency that is in a range from about 0.5 MHz to about 30 MHz. A first received imaging signal of a first ultrasonic transducer of the plurality may have a frequency of about 100 kHz, about 200 kHz, about 300 kHz, about 400 kHz, about 500 kHz, about 650 kHz, about 700 kHz, about 800 kHz, about 850 kHz, about 900 kHz, about 1 MHz, about 2 MHz, about 3 MHz, about 5.5 MHz, about 6 MHz, about 8 MHz, or about 11 MHz. A second received imaging signal of a second ultrasonic transducer of the plurality may have a frequency that is in a range from about 0.5 MHz to about 30 MHz.

In another example, a first transmitted imaging signal of a first ultrasonic transducer of the plurality may have a frequency that is in a range from about 0.5 MHz to about 30 MHz. A second transmitted imaging signal of a second ultrasonic transducer of the plurality may have a frequency that is in a range from about 0.5 MHz to about 30 MHz, but that is different from the frequency of the first transmitted imaging signal. A first received imaging signal of a first ultrasonic transducer of the plurality may have a frequency that is in a range from about 0.5 MHz to about 30 MHz. A second received imaging signal of a second ultrasonic transducer of the plurality may have a frequency that is in a range from about 0.5 MHz to about 30 MHz, but that is different from the frequency of the first received imaging signal.

A third, fourth, fifth, sixth, seventh, eighth, ninth, tenth, eleventh, twelfth, thirteenth, fourteenth, fifteenth, or sixteenth transmitted imaging signal of a third, fourth, fifth, sixth, seventh, eighth, ninth, tenth, eleventh, twelfth, thirteenth, fourteenth, fifteenth, or sixteenth ultrasonic transducer, respectively, may have a frequency that is about 100 kHz, about 200 kHz, about 300 kHz, about 400 kHz, about 500 kHz, about 650 kHz, about 700 kHz, about 800 kHz, about 850 kHz, about 900 kHz, about 1 MHz, about 2 MHz, about 3 MHz, about 5.5 MHz, about 6 MHz, about 8 MHz, or about 11 MHz. The third, fourth, fifth, sixth, seventh, eighth, ninth, tenth, eleventh, twelfth, thirteenth, fourteenth, fifteenth, or sixteenth transmitted imaging signal may have a frequency that is within a range described by any two of the preceding values. The third, fourth, fifth, sixth, seventh, eighth, ninth, tenth, eleventh, twelfth, thirteenth, fourteenth, fifteenth, or sixteenth transmitted imaging signal may have a value that is in a range from about 0.5 MHz to about 30 MHz. The third, fourth, fifth, sixth, seventh, eighth, ninth, tenth, eleventh, twelfth, thirteenth, fourteenth, fifteenth, or sixteenth transmitted imaging signal may have a frequency that is different from one or more of the frequencies of the first and second transmitted imaging signals.

A third, fourth, fifth, sixth, seventh, eighth, ninth, tenth, eleventh, twelfth, thirteenth, fourteenth, fifteenth, or sixteenth received imaging signal of a third, fourth, fifth, sixth, seventh, eighth, ninth, tenth, eleventh, twelfth, thirteenth, fourteenth, fifteenth, or sixteenth ultrasonic transducer, respectively, may have a frequency that is about 100 kHz, about 200 kHz, about 300 kHz, about 400 kHz, about 500 kHz, about 650 kHz, about 700 kHz, about 800 kHz, about 850 kHz, about 900 kHz, about 1 MHz, about 2 MHz, about 3 MHz, about 5.5 MHz, about 6 MHz, about 8 MHz, or about 11 MHz. The third, fourth, fifth, sixth, seventh, eighth, ninth, tenth, eleventh, twelfth, thirteenth, fourteenth, fifteenth, or sixteenth received imaging signal may have a frequency that is within a range described by any two of the preceding values. The third, fourth, fifth, sixth, seventh, eighth, ninth, tenth, eleventh, twelfth, thirteenth, fourteenth, fifteenth, or sixteenth received imaging signal may have a value that is in a range from about 0.5 MHz to about 30 MHz. The third, fourth, fifth, sixth, seventh, eighth, ninth, tenth, eleventh, twelfth, thirteenth, fourteenth, fifteenth, or sixteenth received imaging signal may have a frequency that is different from one or more of the frequencies of the first and second transmitted imaging signals.

Each ultrasonic transducer of the plurality of transducers may transmit transmitted ultrasonic imaging signals or receive received ultrasonic imaging signals within a bandwidth. The first ultrasonic transducer may have a first bandwidth and the second ultrasonic transducer may have a second bandwidth. The first bandwidth and the second bandwidth may overlap. The first bandwidth and the second bandwidth may partially overlap. The first bandwidth and the second bandwidth may not overlap. Similarly, the third, fourth, fifth, sixth, seventh, eighth, ninth, tenth, eleventh, twelfth, thirteenth, fourteenth, fifteenth, or sixteenth ultrasonic transducers may have third, fourth, fifth, sixth, seventh, eighth, ninth, tenth, eleventh, twelfth, thirteenth, fourteenth, fifteenth, or sixteenth bandwidths, respectively. Any one of the first, second, third, fourth, fifth, sixth, seventh, eighth, ninth, tenth, eleventh, twelfth, thirteenth, fourteenth, fifteenth, or sixteenth bandwidths may overlap one another. Any one of the first, second, third, fourth, fifth, sixth, seventh, eighth, ninth, tenth, eleventh, twelfth, thirteenth, fourteenth, fifteenth, or sixteenth bandwidths may partially overlap one another. Any one of the first, second, third, fourth, fifth, sixth, seventh, eighth, ninth, tenth, eleventh, twelfth, thirteenth, fourteenth, fifteenth, or sixteenth bandwidths may not overlap one another.

The received imaging signals may be subjected to preprocessing operations. For instance, a first received imaging signal may form a basis for normalizing other received imaging signals. A second received imaging signal may be normalized by the first received imaging signal. A third, fourth, fifth, sixth, seventh, eighth, ninth, tenth, eleventh, twelfth, thirteenth, fourteenth, fifteenth, or sixteenth received imaging signal may be normalized by the first received imaging signal.

FIG. 2B schematically illustrates simultaneous actuation of the plurality of ultrasonic transducers. The stethoscope device may comprise a transmit (Tx) generator 220. The Tx generator may be a Tx beamformer. The Tx generator may be configured to operate any one of ultrasonic transducers 210A-D to transmit a first, second, third, or fourth transmitted ultrasonic imaging signal, respectively. The Tx generator may operate any two or more of the first, second, third, or fourth ultrasonic imaging transducers simultaneously. The stethoscope device may further comprise an image synthesis module 230. The image synthesis module may comprise a receive (Rx) beamformer. The Rx beamformer may be configured to operate any one of ultrasonic transducers 210A-D to receive a first, second, third, or fourth received ultrasonic imaging signal, respectively. The image synthesis module may subject the received ultrasonic imaging signals to an ultrasonic image reconstruction operation. For instance, the image synthesis module may subject the received ultrasonic imaging signals to a delay and sum operation. The image synthesis module may subject the received ultrasonic imaging signals to any ultrasonic image reconstruction operation. Though shown as operating four ultrasonic imaging transducers in FIG. 2B, the Tx generator may be configured to operate fifth, sixth, seventh, eighth, ninth, tenth, eleventh, twelfth, thirteenth, fourteenth, fifteenth, or sixteenth ultrasonic transducers to transmit fifth, sixth, seventh, eighth, ninth, tenth, eleventh, twelfth, thirteenth, fourteenth, fifteenth, or sixteenth transmitted ultrasonic imaging signals, respectively. The Tx generator may operate any two or more of the first, second, third, fourth, fifth, sixth, seventh, eighth, ninth, tenth, eleventh, twelfth, thirteenth, fourteenth, fifteenth, or sixteenth ultrasonic imaging transducers simultaneously similar, the Rx beamformer may be configured to operate fifth, sixth, seventh, eighth, ninth, tenth, eleventh, twelfth, thirteenth, fourteenth, fifteenth, or sixteenth ultrasonic transducers to transmit fifth, sixth, seventh, eighth, ninth, tenth, eleventh, twelfth, thirteenth, fourteenth, fifteenth, or sixteenth transmitted ultrasonic imaging signals, respectively.

The Tx generator may be configured to operate any one of the first, second, third, fourth, fifth, sixth, seventh, eighth, ninth, tenth, eleventh, twelfth, thirteenth, fourteenth, fifteenth, or sixteenth ultrasonic transducers to transmit in sequence. FIG. 3 shows operation of the ultrasonic transducers in sequence. As depicted in FIG. 3, an ultrasonic transducer that is transmitting a transmitted ultrasonic signal at a given time is indicated by a solid box. An ultrasonic transducer that is not transmitting at a given time is indicated by a dashed box.

Figure 3A:
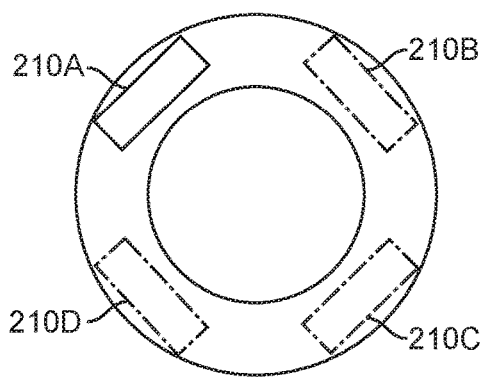
FIG. 3A schematically illustrates actuation of a first ultrasonic transducer of the plurality of ultrasonic transducers at a first time point.

FIG. 3A schematically illustrates actuation of a first ultrasonic transducer of the plurality of ultrasonic transducers at a first time point. During the first point in time, ultrasonic imaging transducer 210A may transmit a first transmitted ultrasonic imaging signal. During the first point in time, ultrasonic imaging transducers 210B, 210C, and 210D may not transmit. During the first point in time, ultrasonic imaging transducers 210B, 210C, and 210D may be operated in a receive mode, so as to receive second, third, and fourth received ultrasonic imaging signals, respectively.

Figure 3B:
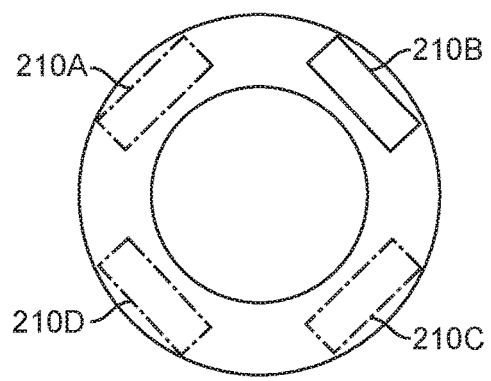
FIG. 3B schematically illustrates actuation of a second ultrasonic transducer of the plurality of ultrasonic transducers at a second time point.

FIG. 3B schematically illustrates actuation of a second ultrasonic transducer of the plurality of ultrasonic transducers at a second time point. The second point in time may be different from the first point in time. During the second point in time, ultrasonic imaging transducer 210B may transmit a second transmitted ultrasonic imaging signal. During the second point in time, ultrasonic imaging transducers 210A, 210C, and 210D may not transmit. During the second point in time, ultrasonic imaging transducers 210A, 210C, and 210D may be operated in a receive mode, so as to receive first, second, and fourth received ultrasonic imaging signals, respectively.

Figure 3C:
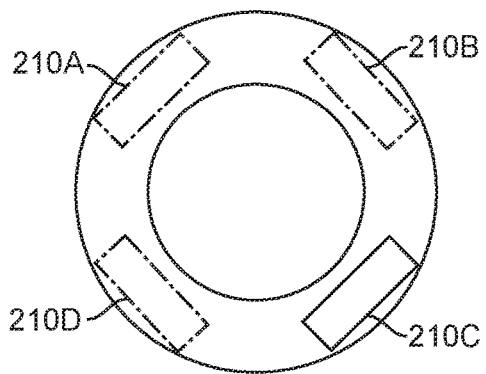
FIG. 3C schematically illustrates actuation of a third ultrasonic transducer of the plurality of ultrasonic transducers at a third time point.

FIG. 3C schematically illustrates actuation of a third ultrasonic transducer of the plurality of ultrasonic transducers at a third time point. The third point in time may be different from the first point in time and the second point in time. During the third point in time, ultrasonic imaging transducer 210C may transmit a third transmitted ultrasonic imaging signal. During the third point in time, ultrasonic imaging transducers 210A, 210B, and 210D may not transmit. During the third point in time, ultrasonic imaging transducers 210A, 210B, and 210D may be operated in a receive mode, so as to receive first, second, and fourth received ultrasonic imaging signals, respectively.

Figure 3D:
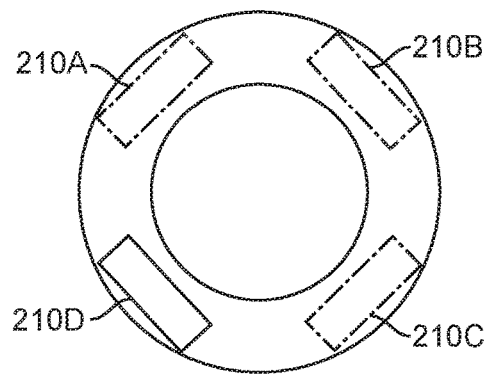
FIG. 3D schematically illustrates actuation of a fourth ultrasonic transducer of the plurality of ultrasonic transducers at a fourth time point.

FIG. 3D schematically illustrates actuation of a fourth ultrasonic transducer of the plurality of ultrasonic transducers at a fourth time point. The fourth point in time may be different from the first point in time, the second point in time, and the third point in time. During the fourth point in time, ultrasonic imaging transducer 210D may transmit a fourth transmitted ultrasonic imaging signal. During the fourth point in time, ultrasonic imaging transducers 210A, 210B, and 210C may not transmit. During the fourth point in time, ultrasonic imaging transducers 210A, 210B, and 210C may be operated in a receive mode, so as to receive first, second, and third received ultrasonic imaging signals, respectively.

The ultrasonic imaging transducers may be operated in any order. For instance, any one of ultrasonic imaging transducers 210B, 210C, and 210D may be operated in a transmit mode at the first point in time while the other ultrasonic imaging transducers are operated in a receive mode at the first point in time. Any one of ultrasonic imaging transducers 210A, 210C, and 210D may be operated in a transmit mode at the second point in time while the other ultrasonic imaging transducers are operated in a receive mode at the second point in time. Any one of ultrasonic imaging transducers 210A, 210B, and 210D may be operated in a transmit mode at the third point in time while the other ultrasonic imaging transducers are operated in a receive mode at the third point in time. Any one of ultrasonic imaging transducers 210A, 210B, and 210C may be operated in a transmit mode at the fourth point in time while the other ultrasonic imaging transducers are operated in a receive mode at the fourth point in time.

Any two of the ultrasonic imaging transducers may be operated in a transmit mode at any given point in time while any other two of the ultrasonic imaging transducers are operated in a receive mode at that point in time. Any three of the ultrasonic imaging transducers may be operated in a transmit mode at any given point in time while the other ultrasonic imaging transduces is operated in a receive mode at that point in time.

Figure 4:
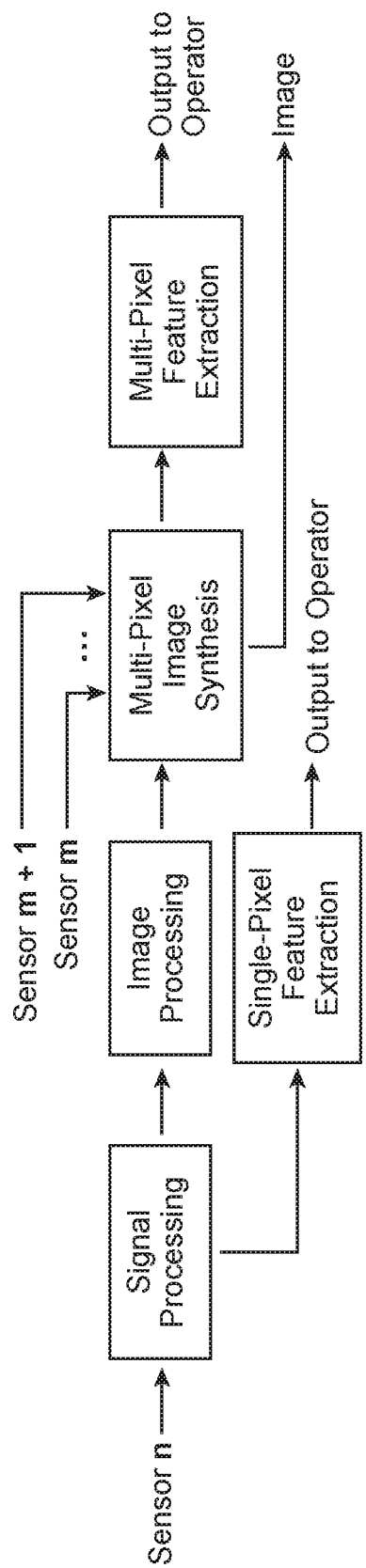
FIG. 4 schematically illustrates a method of forming ultrasonic images from a plurality of ultrasonic transducers.

FIG. 4 schematically illustrates a method of forming ultrasonic images from a plurality of ultrasonic transducers. The method may utilize measurements from a plurality of ultrasonic imaging sensors. The method may utilize single-pixel and multi-pixel image processing techniques. In the single-pixel case, an n-th ultrasonic imaging measurement (where n is a positive integer) may be input to a signal processing unit. The signal processing unit may apply any ultrasonic signal processing procedure to the n-th ultrasonic imaging measurement. The signal processing unit may output a signal processed measurement to an image processing unit and to a single-pixel feature extraction unit. The image processing unit may apply any ultrasonic image processing procedure. The single-pixel feature extraction unit may apply any ultrasonic single-pixel feature extraction procedure. The single-pixel feature extraction unit may output an extracted feature to an operator.

In the multi-pixel case, an m-th and an (m+1)-th (where m and m+1 are positive integers) ultrasonic imaging measurement may be input to a multi-pixel image synthesis unit and to a multi-pixel feature extraction unit. The image synthesis unit may apply any ultrasonic image synthesis procedure. The multi-pixel feature extraction unit may apply any ultrasonic multi-pixel feature extraction procedure. The multi-feature extraction unit may output an extracted feature to an operator.

In the multi-pixel case, image processing methods such as 2-dimensional smoothing filters, Harr filters, Gaussian filters, and integrators may be used to improve the recorded image. Furthermore, each pixel may be filtered in the time-domain to accentuate signal features. A single or multiple Butterworth, Chebyshev, and elliptic filters can be used to suppress noise and enhance feature extraction.

Figure 17:
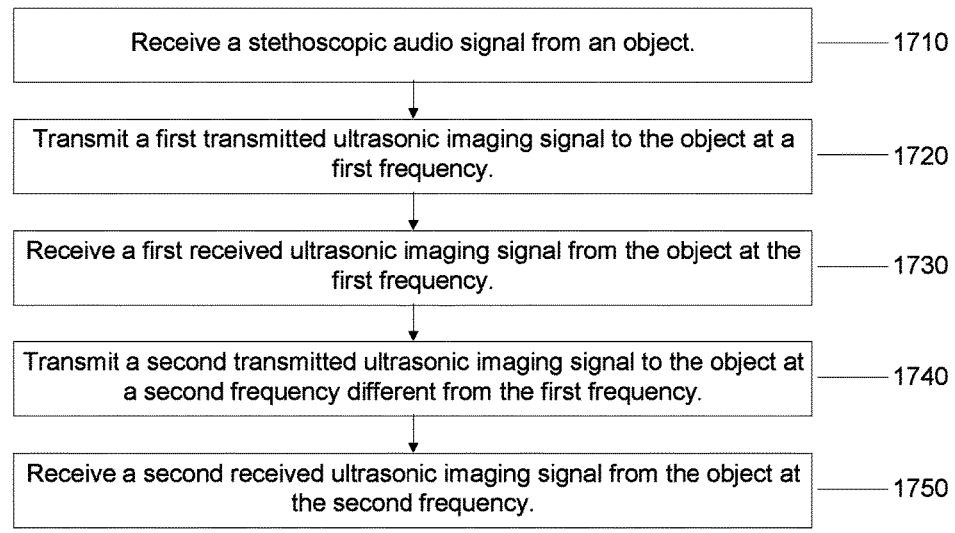
FIG. 17 illustrates a method for receiving a stethoscopic audio signal, simultaneously transmitting first and second ultrasonic imaging signals, and receiving first and second ultrasonic imaging signals.

FIG. 17 illustrates a method 1700 for receiving a stethoscopic audio signal, simultaneously transmitting first and second ultrasonic imaging signals, and receiving first and second ultrasonic imaging signals.

In a first operation 1710, a stethoscopic audio signal is received from an object. The stethoscopic audio signal may be received by a stethoscope head comprising a mechanical diaphragm, as described herein.

In a second operation 1720, a first transmitted ultrasonic imaging signal is transmitted to the object at a first frequency. The first transmitted ultrasonic imaging signal may be transmitted by a first ultrasonic transducer, as described herein.

In a third operation 1730, a first received ultrasonic imaging signal is received from the object. The first received ultrasonic imaging signal may be received by a first ultrasonic transducer, as described herein.

In a fourth operation 1740, a second transmitted ultrasonic imaging signal is transmitted to the object at a second frequency. The second transmitted ultrasonic imaging signal may be transmitted by a second ultrasonic transducer, as described herein. The second transmitted ultrasonic imaging signal may be transmitted simultaneously with the first transmitted ultrasonic imaging signal, as described herein.

In a fifth operation 1750, a second received ultrasonic imaging signal is received from the object. The second received ultrasonic imaging signal may be received by a second ultrasonic transducer, as described herein. The second received ultrasonic imaging signal may be received simultaneously with the first transmitted ultrasonic imaging signal, as described herein.

The method 1700 may further comprise an operation (not shown in FIG. 17) of detecting a non-stethoscopic, non-ultrasonic signal. The non-stethoscopic, non-ultrasonic signal may be detected by a non-stethoscopic, non-ultrasonic sensor, as described herein.

The method 1700 may be implemented by any of the devices described herein, such as the devices described herein with respect to FIG. 1, FIG. 2, FIG. 3, or FIG. 4.

Many variations, alterations, and adaptations based on the method 1700 provided herein are possible. For example, the order of the operations of the method 1700 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated and some of the operations may be manual.

FIG. 5A schematically illustrates a side view of a stethoscope head comprising a mechanical diaphragm, a plurality of ultrasound transducers, and a plurality of non-stethoscopic, non-ultrasonic sensors. The stethoscope device may comprise the mechanical diaphragm 200 and plurality of ultrasonic transducers 210A-D described herein.

FIG. 5B schematically illustrates a perspective view of a stethoscope head comprising a mechanical diaphragm, a plurality of ultrasound transducers, and a plurality of non-stethoscopic, non-ultrasonic sensors. In addition to the mechanical diaphragm and the plurality of ultrasonic transducers, the stethoscope head may comprise one or more non-stethoscopic, non-ultrasonic sensors. The non-stethoscopic, non-ultrasonic sensors may detect one or more non-stethoscopic, non-ultrasonic signals. As shown in FIG. 5B, may comprise a first light source 510 and a first photodetector 520. The first light source may be a light emitting diode (LED) or a laser. The laser may be a semiconductor laser, such as a vertical cavity surface emitting laser (VCSEL). The first photodetector may be a photodiode, an avalanche photodiode, a photodiode array, a spectrometer, a charge coupled device (CCD) camera, a complementary metal oxide semiconductor (CMOS) camera, or any other photodetector.

The first light source and first photodetector may be configured to operate as a first pulse oximeter. The pulse oximeter may be configured to operate as a reflectance pulse oximeter. The first light source may direct light to the subject's skin, such as to the skin of the subject's fingertip, finger, hand, arm, or any other location on the subject's skin. The light may be reflected by the subject's skin and detected by the first light detector. Different wavelengths of light incident on the subject's skin may be absorbed to different extents. The absorption of the different wavelengths may be indicative of the subject's oxygen saturation ($spO_2$).

The stethoscope head may further comprise a second light source and a second photodetector. The second light source and second photodetector may be similar to the first light source and the first photodetector, respectively. The second light source and second photodetector may be configured to operate as a second pulse oximeter. The second pulse oximeter may be similar to the first pulse oximeter. In some cases, the first light source, first photodetector, the second light source, and the second photodetector may be configured to operate as a single pulse oximeter. For instance, the first and second light sources may each emit first and second monochromatic light, respectively, having different wavelengths. The first and second photodetectors may measure the absorbance of the first and second monochromatic light, respectively. The measurements may allow a determination of the subject's $spO_2$.

The stethoscope head may comprise 1, 2, 3, 4, 5, 6, 7, 8, 9, 10, 11, 12, 13, 14, 15, 16, or more than 16 non-stethoscopic, non-ultrasonic sensors. Each non-stethoscopic, non-ultrasonic sensor may be any one of a non-stethoscopic audio sensor, a temperature sensor, an optic sensor, an electrical sensor, or an electrochemical sensor. The non-stethoscopic, non-ultrasonic sensor may detect a signal corresponding to a subject's body temperature, a subject's respiration rate, a subject's respiration quality, a subject's respiration pathology, a subject's blood pressure, a subject's blood glucose concentration, or a subject's blood oxygenation saturation ($spO_2$).

Figure 6A:
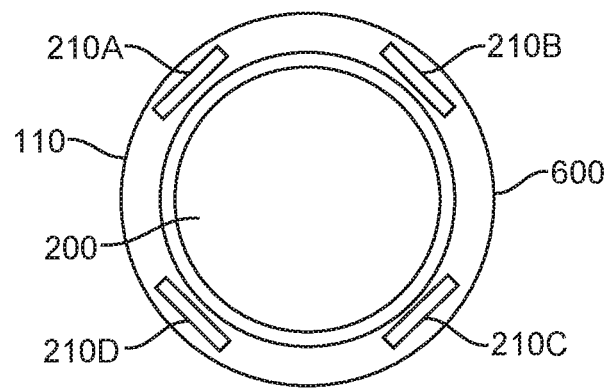
FIG. 6A schematically illustrates a top view of a stethoscope head comprising a body, an impedance matching substrate, and a user interface.

FIG. 6A schematically illustrates a top view of a stethoscope head comprising a body, an impedance matching substrate, and a user interface. The stethoscope head 110 may comprise the mechanical diaphragm and the one or more ultrasonic transducers described herein. The stethoscope head may further comprise an impedance matching substrate 600. The impedance matching substrate may be composed of an impedance matching material. The impedance matching material may increase the efficiency with which any one of the first, second, third, fourth, fifth, sixth, seventh, eighth, ninth, tenth, eleventh, twelfth, thirteenth, fourteenth, fifteenth, or sixteenth transmitted or received ultrasonic imaging signals are passed between the corresponding ultrasonic transducer and a sample under examination.

Figure 6B:
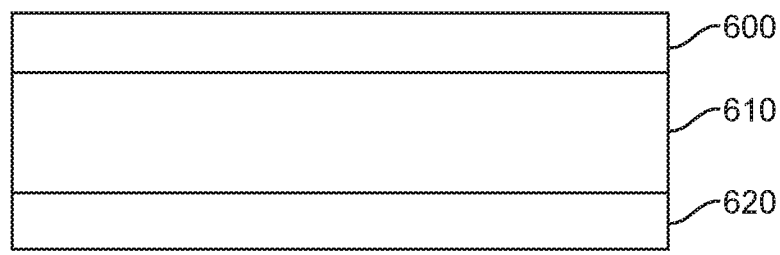
FIG. 6B schematically illustrates a side view of a stethoscope head comprising a body, an impedance matching substrate, and a user interface.

FIG. 6B schematically illustrates a side view of a stethoscope head comprising a body, an impedance matching substrate, and a user interface. On a top layer, the stethoscope head may comprise the impedance matching substrate 600.

In a middle layer, the stethoscope head may comprise a body 610. The body may comprise a battery. The battery may allow one or more of the components of the stethoscope device described herein to operate without access to an external power source. The body may comprise a power connector. The power connector may be configured to receive electrical power from an external power source, such as an electrical outlet. The power connector may allow one or more of the components of the stethoscope device described herein to operate while powered by an external power source. The power connector may allow the battery to be charged, either while one or more of the components described herein are in operation or while the stethoscope device is not in use. The power connector may be an inductive power coil.

In a bottom layer, the stethoscope head may comprise a control 620, as described herein.

Figure 6C:
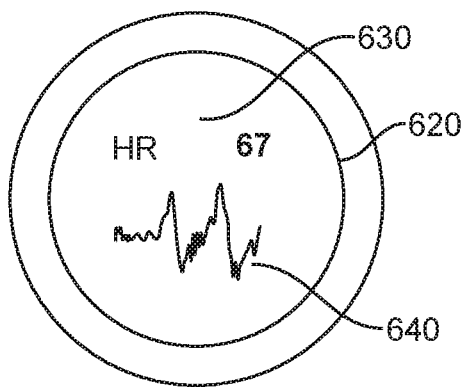
FIG. 6C schematically illustrates a bottom view of a stethoscope head comprising a body, an impedance matching substrate, and a user interface.

FIG. 6C schematically illustrates a bottom view of a stethoscope head comprising a body, an impedance matching substrate, and a user interface. The control 620 may allow the stethoscope device to be operated in a variety of modes. For instance, the control may allow the stethoscope device to be operated in a stethoscope mode. The stethoscope mode may allow a user to use the stethoscope device as a traditional stethoscope, providing the user the ability to listen to sounds associated with biological processes through the stethoscope while one or more of the non-stethoscopic sensors (such as the plurality of ultrasonic transducers or any one of the non-stethoscopic, non-ultrasonic sensors) are powered off or operating in a standby mode. The control may allow the stethoscope device to be operated in an ultrasonic imaging mode. The ultrasonic imaging mode may allow a user to use the stethoscope device as an ultrasonic imaging device, providing the user the ability to ultrasonic images of an internal structure of a subject. In the ultrasonic imaging mode, one or more of the non-stethoscopic, non-ultrasonic sensors may be powered off or operating in a standby mode. In the ultrasonic imaging mode, all of the non-stethoscopic, non-ultrasonic sensors may be powered on. The control may allow the stethoscope device to be operated in a non-stethoscopic, non-ultrasonic mode. The non-stethoscopic, non-ultrasonic mode may allow a user to use the stethoscope device to obtain any non-stethoscopic, non-ultrasonic sensor data described herein from a subject. In the non-stethoscopic, non-ultrasonic mode, one or more of the ultrasonic transducers may be powered off or operating in a standby mode. In the ultrasonic imaging mode, all of the ultrasonic transducers may be powered on. The stethoscope device may be operated in a mode in which more than one sensor component (such as the mechanical diaphragm, one or more ultrasonic transducers, and one or more non-stethoscopic, non-ultrasonic sensors) are operated together to obtain stethoscopic, ultrasonic, and non-stethoscopic, non-ultrasonic sensor data simultaneously or in any possible sequence.

The control may comprise a user interface. The user interface may be configured to provide a user with feedback based on one or more of a stethoscopic signal, an ultrasonic imaging signal, or a non-stethoscopic, non-ultrasonic signal described herein. The user interface may comprise a display. The user interface may display one or more of a stethoscopic signal, an ultrasonic imaging signal, or a non-stethoscopic, non-ultrasonic signal described herein. For instance, the user interface may display a heart rate 630 of a subject that may be detected by a heart rate sensor described herein. The user interface may display a graph 640 of the subject's heart rate over time. The user device may display an ultrasonic image or a representation of any non-stethoscopic, non-ultrasonic signal obtained by any non-stethoscopic, non-ultrasonic sensor described herein.

The user interface may comprise a touchscreen device. The touchscreen device may function as a display, as described herein. The touchscreen device may also allow a user to direct commands to the stethoscope device. For instance, the touchscreen device may allow a user of the stethoscope device to select any one of the operating modes of the stethoscope device described herein.

The stethoscope device may further comprise a networking modality. The networking modality may be a wired networking modality. For instance, the stethoscope device may comprise an Ethernet adaptor or any other wired networking modality. The networking modality may be a wireless networking modality. The wireless networking modality may comprise an inductive power coil for transmitting and receiving data. The stethoscope device may comprise a wireless transceiver. For instance, the stethoscope device may comprise a Wi-Fi transceiver such as an 802.11a transceiver, 802.11b transceiver, 802.11g transceiver, 802.11n transceiver, 802.11ac transceiver, 802.11ad transceiver, 802.11af transceiver, 802.11ah transceiver, 80.211ai transceiver, 802.11aj transceiver, 802.11aq transceiver, 802.11ax transceiver, 802.11ay transceiver, or any other Wi-Fi transceiver. The wireless networking modality may comprise a cellular transceiver such as a code division multiple access (CDMA) transceiver, a global system for mobiles (GSM) transceiver, a third-generation (3G) cellular transceiver, a fourth-generation (4G) cellular transceiver, a long-term evolution (LTE) cellular transceiver, a fifth-generation (5G) cellular transceiver, or any other cellular transceiver. The wireless networking modality may comprise a Bluetooth transceiver. The wireless networking modality may comprise any other wireless networking modality. The wireless networking modality may be configured to communicate one or more of a stethoscopic signal, a received ultrasonic signal, or a non-stethoscopic, non-ultrasonic signal described herein to a peripheral device. For instance, the wireless networking modality may be configured to communicate one or more of the signals to a smartphone, smartwatch, or other smart device, a tablet, a laptop, or other computing device, or a server, such as a cloud-based server.

The stethoscope device may comprise a microphone and a speaker. The microphone and speaker may enable communication between a user of the stethoscope device and the stethoscope device itself. The speaker may allow a user to receive the results of one or more of a stethoscopic measurement, an ultrasonic imaging measurement, or a non-stethoscopic, non-ultrasonic measurement via an audio announcement from the stethoscope device. The microphone may allow a user to provide commands to the stethoscope device orally. The microphone may be coupled to a natural language processing system to parse commands spoken by the user to the stethoscope device.

Figure 7:
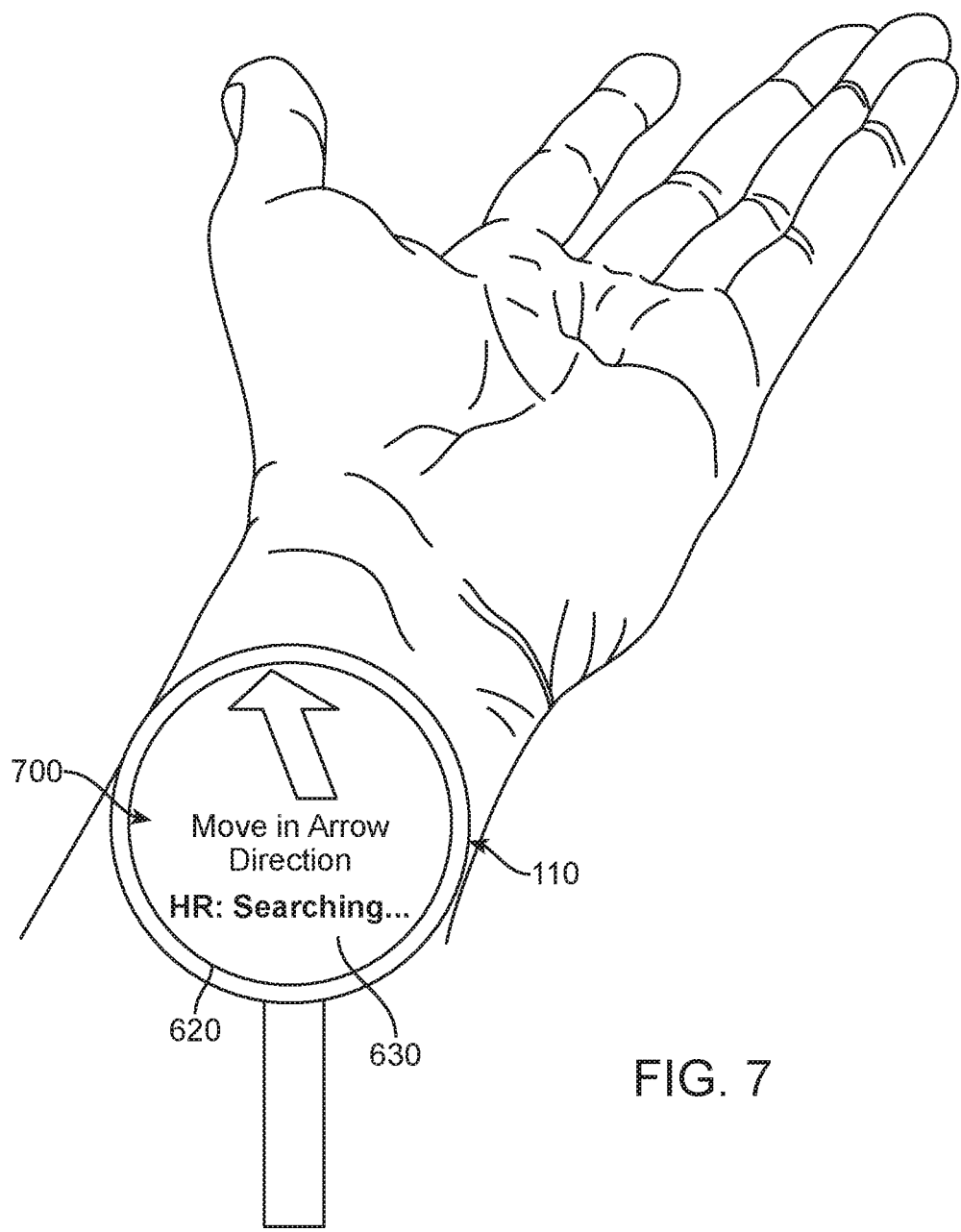
FIG. 7 schematically illustrates use of a stethoscope head comprising a user interface in an interactive imaging mode.

FIG. 7 schematically illustrates use of a stethoscope head comprising a user interface in an interactive imaging mode. The stethoscope device may be used to search for a pulse of a subject. When the stethoscope device fails to detect a strong pulse signal, the stethoscope device may indicate to a user that the stethoscope head should be moved to a different location. The display 520 may indicate that a heart rate 530 is yet to be determined. The display may comprise an indicator 800 that the stethoscope head should be moved in a particular direction. For instance, the display may show an arrow pointing in the direction that the stethoscope head should be moved.

Figure 18:
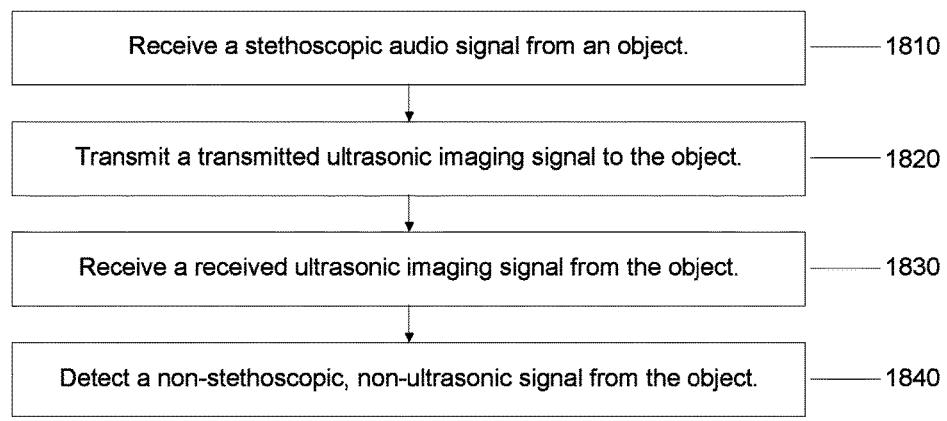
FIG. 18 illustrates a method for receiving a stethoscopic audio signal, transmitting and receiving an ultrasonic imaging signal, and detecting a non-stethoscopic, non-ultrasonic imaging signal.

FIG. 18 illustrates a method 1800 for receiving a stethoscopic audio signal, transmitting and receiving an ultrasonic imaging signal, and detecting a non-stethoscopic, non-ultrasonic imaging signal.

In a first operation 1810, a stethoscopic audio signal is received from an object. The stethoscopic audio signal may be received by a stethoscope head comprising a mechanical diaphragm, as described herein.

In a second operation 1820, a transmitted ultrasonic imaging signal is transmitted to the object. The transmitted ultrasonic imaging signal may be transmitted by an ultrasonic transducer, as described herein.

In a third operation 1830, a received ultrasonic imaging signal is received from the object. The received ultrasonic imaging signal may be received by an ultrasonic transducer, as described herein.

In a fourth operation 1840, a non-stethoscopic, non-ultrasonic signal is detected. The non-stethoscopic, non-ultrasonic signal may be detected by a non-stethoscopic, non-ultrasonic sensor, as described herein.

The method 1800 may be implemented by any of the devices described herein, such as the devices described herein with respect to FIG. 5, FIG. 6, or FIG. 7.

Many variations, alterations, and adaptations based on the method 1800 provided herein are possible. For example, the order of the operations of the method 1800 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated and some of the operations may be manual.

Any one of the stethoscopic signals, ultrasonic imaging signals, or non-stethoscopic, non-ultrasonic signals described herein may be correlated using a model. For instance, the stethoscope device described herein may correlate a first and second signal. The first signal may be a stethoscopic signal, an ultrasonic imaging signal, or a non-stethoscopic, non-ultrasonic signal. The second signal may be a stethoscopic signal, an ultrasonic imaging signal, or a non-stethoscopic, non-ultrasonic signal. The first and second signals may be correlated to generate one or more extracted feature parameters. Third, fourth, fifth, sixth, seventh, eighth, ninth, tenth, eleventh, twelfth, thirteenth, fourteenth, fifteenth, or sixteenth signals may each be a stethoscopic signal, an ultrasonic imaging signal, or a non-stethoscopic, non-ultrasonic signal and may be further correlated with the first and second signals to generate one or more extracted feature parameters. The extracted feature parameters may be indicative of one or more physiological parameters, such as a heart rate, blood pressure, blood oxygenation, or any other physiological parameter described herein.

The model may correlate the first and second signals by first convolving each of the first and second signals with a weighting function. The first signal may be convolved by a first weighting function to form a first weighted signal. The second signal may be convolved by a second weighting function to form a second weighted signal. The first and second weighted signals may then be correlated (such as by auto-correlation or cross-correlation) to generate the extracted feature parameters. The model may convolve third, fourth, fifth, sixth, seventh, eighth, ninth, tenth, eleventh, twelfth, thirteenth, fourteenth, fifteenth, or sixteenth signals with third, fourth, fifth, sixth, seventh, eighth, ninth, tenth, eleventh, twelfth, thirteenth, fourteenth, fifteenth, or sixteenth weighting functions, respectively, to form third, fourth, fifth, sixth, seventh, eighth, ninth, tenth, eleventh, twelfth, thirteenth, fourteenth, fifteenth, or sixteenth weighted signals, respectively. The third, fourth, fifth, sixth, seventh, eighth, ninth, tenth, eleventh, twelfth, thirteenth, fourteenth, fifteenth, or sixteenth weighted signals may be correlated with the first and second weighted signals to generate the extracted feature parameters.

The model may correlate the first and second signals by applying a mathematical transformation to each of the first and second signals. For instance, each of the first and second imaging signals may be transformed by a Fourier transform, a Fourier integral transform, a Fourier series transform, a Z-transform, a wavelet transform, a cosine series transform, a sine series transform, a Taylor series transform, a Laurent series transform, a Laplace transform, a Hadamard transform, or any other mathematical transform. The first signal may be transformed by a first mathematical transform to form a first transformed signal. The second signal may be transformed by a second mathematical transform to form a second transformed signal. The first and second transformed signals may then be correlated (such as by auto-correlation or cross-correlation) to generate the extracted feature parameters. The model may transform third, fourth, fifth, sixth, seventh, eighth, ninth, tenth, eleventh, twelfth, thirteenth, fourteenth, fifteenth, or sixteenth signals with third, fourth, fifth, sixth, seventh, eighth, ninth, tenth, eleventh, twelfth, thirteenth, fourteenth, fifteenth, or sixteenth mathematical transforms, respectively, to form third, fourth, fifth, sixth, seventh, eighth, ninth, tenth, eleventh, twelfth, thirteenth, fourteenth, fifteenth, or sixteenth transformed signals, respectively. The third, fourth, fifth, sixth, seventh, eighth, ninth, tenth, eleventh, twelfth, thirteenth, fourteenth, fifteenth, or sixteenth transformed signals may be correlated with the first and second transformed signals to generate the extracted feature parameters.

The model may correlate the first and second signals by encoding and mapping the first and second signals to a set of extracted features using a machine learning technique. The model may correlate third, fourth, fifth, sixth, seventh, eighth, ninth, tenth, eleventh, twelfth, thirteenth, fourteenth, fifteenth, or sixteenth signals with the first and second transformed signals by encoding and mapping the first, second, third, fourth, fifth, sixth, seventh, eighth, ninth, tenth, eleventh, twelfth, thirteenth, fourteenth, fifteenth, or sixteenth signals to a set of extracted features using a machine learning technique. The model may correlate any number of transformed signals.

Figure 8:
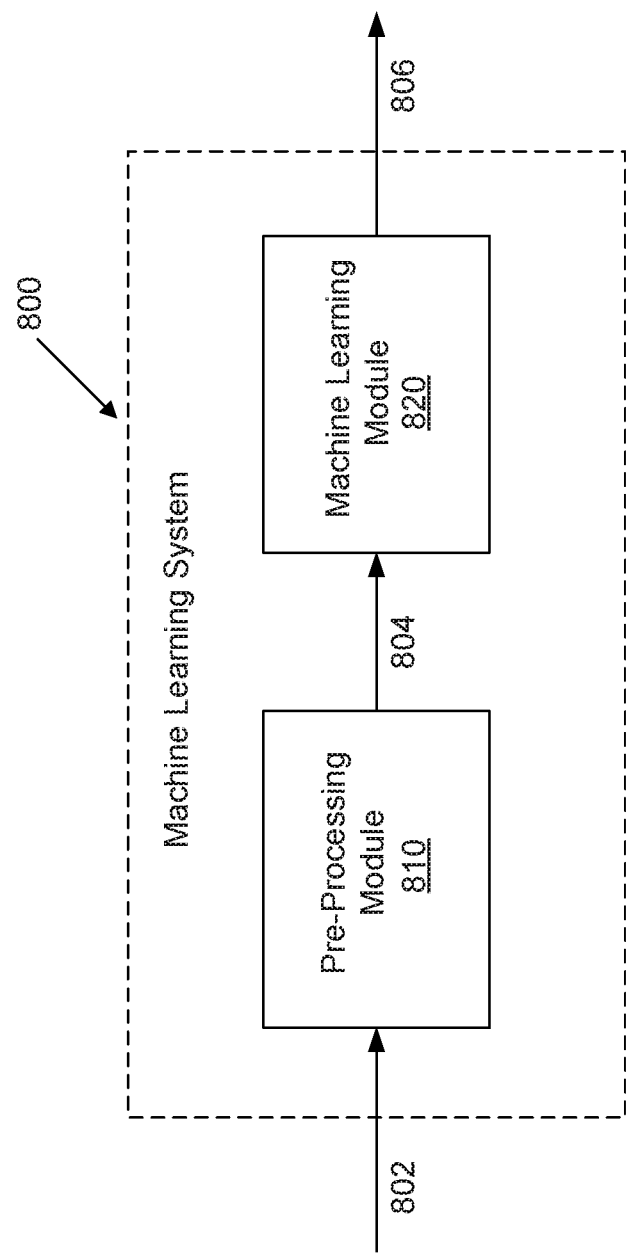
FIG. 8 illustrates a schematic block diagram of a machine learning system comprising a pre-processing module and a machine learning module.

FIG. 8 illustrates a schematic block diagram of a machine learning system comprising a pre-processing module and a machine learning module. The machine learning system 800 may comprise a pre-processing module 810 and a machine learning module (also referred to as an approximator or an approximation module) 820. The components within the machine learning system may be operatively connected to one another via a network or any type of communication link that allows transmission of data from one component to another. The machine learning system may be implemented using software, hardware, or a combination of software and hardware in one or more of the components of the systems and methods described herein.

Physiological information 802 may be collected using one or more of the mechanical diaphragm, ultrasonic imaging transducers, or non-stethoscopic, non-ultrasonic sensors of the stethoscope device described herein. The pre-processing module 810 may be configured to subject the physiological information to pre-processing. The pre-processing module may remove artifacts produced, for instance, by the mechanical diaphragm, ultrasonic imaging transducers, or non-stethoscopic, non-ultrasonic sensors. The pre-processing module may correct the microscope images for mechanical noise, such as movement of the stethoscope device. The pre-processing module may correct for non-uniform detection sensitivities of the ultrasonic transducers. The pre-processing module may apply smoothing filters to reduce sensor noise from any one of the mechanical diaphragm, ultrasonic imaging transducers, or non-stethoscopic, non-ultrasonic sensors. The pre-processing module may apply any noise reduction or signal enhancement methods to increase the signal-to-noise ration of any signals obtained by the mechanical diaphragm, ultrasonic imaging transducers, or non-stethoscopic, non-ultrasonic sensors. The pre-processing module may be configured to output pre-processed physiological information 804.

The machine learning module 820 may be configured to process the pre-processed physiological information 804 to extract a meaningful representation of the physiological information. For example, the machine learning module may generate a set of minimal physiological data 106 from the pre-processed physiological information. The minimal physiological data may correspond to a highly compressed meaningful representation of a stream of physiological information. The minimal physiological data may correspond to one or more clinically relevant feature parameters described herein, such as a body temperature, a respiration rate, a respiration quality, a respiration pathology, a blood pressure, a blood glucose concentration, a blood gas concentration, a blood oxygenation saturation (spO2), or any other clinically relevant feature parameters.

In the machine learning module, a new representation for the physiological data may be found where the new representation has characteristics such as low dimensionality, sparse coding, and/or invariance to certain noise or signal transformations. For example, the approximator may find representations that are insensitive (or less sensitive) to signal transformations that occur when the stethoscope device moves relative to signal sources, such as due to mild mechanical disturbance. The machine learning module may account for changes in the sensor responses over time, for instance due to aging of components in the stethoscope device, fluctuations in transmitted ultrasonic power delivered to the sample, and other phenomena which alter the signals detected by the stethoscope device over time. In each of the above cases, one or more deterministic transformations may be applied to the physiological data, and depending on the representational scheme selected by the approximator, these transformations may or may not result in a change in the output of the machine learning system. By training the approximator to respond invariantly in the face of predictable and deterministic perturbations to its input, these low-level changes may be made invisible to the high-level output of the machine learning system.

The above objectives may be achieved by applying one or more machine learning methods that decompose their input according to a self-learned (unsupervised) set of bases, while incorporating certain constraints or priors in said decomposition. Some of the constraints used may include constraints which are aware of facts about the underlying physiological state space.

The machine learning module may also be implemented by explicitly modeling the data stream using probabilistic graphic models and using matrix methods such as L1/L2 lasso regularization (for finding sparse solutions) or eigenvector based approaches to find low rank approximations of the matrix. The machine learning module may also be implemented using neural networks such as autoencoders, stacked autoencoders, denoising autoencoders, deep belief networks, etc.

The approximation stage may be implemented as a multi-layered neural network where the output of each hidden layer of a plurality of hidden layers attempts to reconstruct the input from the preceding layer with some constraint imposed or where its input has been either corrupted or transformed in a way to favor invariant representation. This may include so-called "deep belief networks" or "stacked auto-encoders". The inner layers may be constrained by means of limiting what values their weights may take, or by limiting how quickly or tightly their weights may settle towards the optimum as a form of a regularization strategy, etc. The multiple inner layers may lead to increasing degrees of abstraction and invariance to small perturbations of the signal. The layers may be updated separately, allowing for changes in physiological information over time to be learned by retraining of a low-level layer while the output of the higher level layers remain the same.

The training phase to determine the parameters for the algorithm implemented at this stage may occur offline, but use of the approximator may be in real time. Updating of weights/coefficients may then occur regularly and while the approximator is in use.

Figure 9:
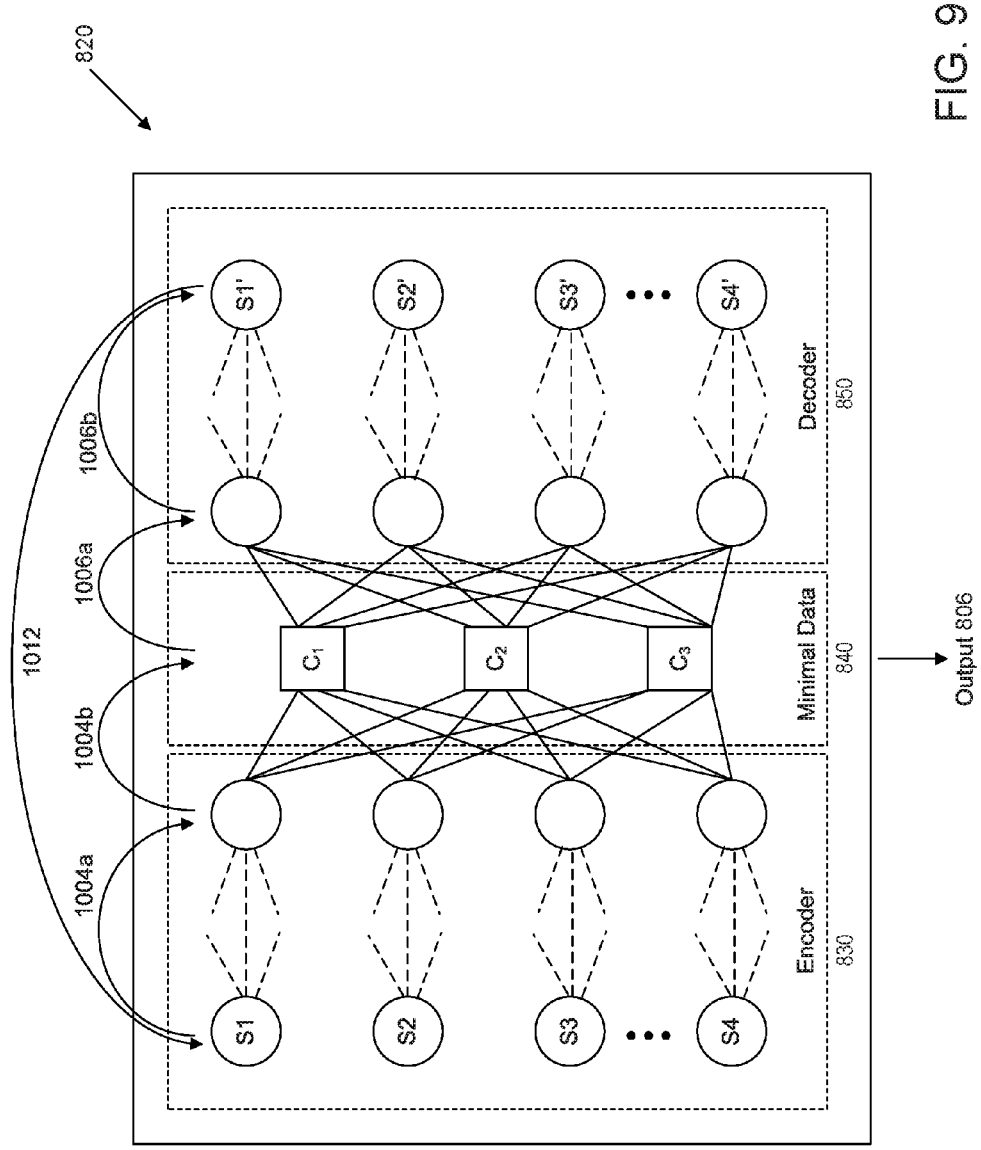
FIG. 9 illustrates an exemplary multi-layer autoencoder configured to convert a set of pre-processed physiological information from the pre-processing module into minimal physiological data.

FIG. 9 illustrates an exemplary multi-layer autoencoder configured to convert a set of pre-processed physiological information from the pre-processing module into minimal physiological data, in accordance with some embodiments. The machine learning module 820 may comprise an encoder 830 and a decoder 850. The machine learning module may be configured to output minimal physiological data 840. The minimal physiological data may correspond to the innermost layer of the autoencoder.

In some embodiments, the encoder may further comprise a plurality of encoding layers. Each encoding layer may comprise a plurality of nodes bearing a plurality of numerical weights. Similarly, the decoder may further comprise a plurality of decoding layers. Each decoding layer may comprise a plurality of nodes bearing a plurality of numerical weights. The innermost layer of the machine learning module may be the minimal physiological data. The minimal physiological data may comprise a plurality of nodes bearing numerical weights. The minimal physiological data may specify an abstract yet meaningful representation of physiological information within the machine learning architecture shown. In some embodiments, the machine learning module may comprise an autoencoder, such that the output of the decoder is identical to and provided as the input to the encoder. In some embodiments, the autoencoder may be a multi-layer autoencoder.

The encoder may be configured to receive an input comprising the set of pre-processed physiological information 804 from the pre-processing module. The set of pre-processed physiological information may be arranged as a vector S. The first layer of the encoder may be configured to reduce the dimensionality of the set of pre-processed physiological information by applying a transformation to the vector S. In some embodiments, the transformation may be a linear transformation. In other embodiments, the transformation may be a nonlinear transformation. The transformation may produce an output vector T having reduced dimensionality relative to the vector S, based on a function o, a matrix W of weights at each node in the layer, and another vector b:

$$T = a(WS + b) \quad \text{(Equation 1)}$$

The vector T may then be input to the second layer. Each successive encoding layer may apply matrix transformations of the same form as Equation (1), with a successive reduction in dimensionality at each layer until the innermost layer (the minimal physiological data) is reached.

The decoder may be configured to undo the abovementioned reduction in dimensionality in order to calculate the accuracy of the matrices of weights applied at each layer of the encoder. The minimal physiological data may be input to the first layer of the decoder, which may apply a linear transformation to increase dimensionality. Each successive decoding layer may apply further matrix transformations, until an output S' from the encoding layer of the same dimensionality as the original input set S is reached.

The initial weights of each node in each layer of the encoder, decoder, and minimal physiological data may be selected based on any predetermined procedure. The series of matrix transformations may be applied to map the input S at the first encoding layer to the output S' at the final decoding layer. An error function, such as an L1 error or an L2 error, may be calculated from S and S'. An algorithm, such as backpropagation, may then be applied to update the weights at each node in each layer of the encoder, decoder, and minimal physiological data. The algorithm may be applied iteratively until the error function assessed at the output of the decoder reaches a minimum value.

In some embodiments, sparsity restraints may be applied on some or all of the layers in the machine learning module.

The machine learning module may be configured to distill a dataset having high dimensionality into a minimal set of numerical values that still maintains the essential features of the dataset without redundancy. This set of numerical values then forms the minimal physiological data corresponding to a given set of physiological information.

In some embodiments, the autoencoder can be designed in multiple layers in order to improve its robustness against changes in the stethoscope system. This may also allow specific layers to be retrained in isolation to reduce the computational overhead of adapting the system to changing recording conditions (e.g., physical changes to or variations in sensors of the stethoscope system).

Accordingly, the machine learning system described herein may serve as a pipeline for processing physiological data comprising information from numerous physiological processes. The system may transform the image data to a higher-level symbol stream which represents salient features of the physiological data.

Figure 10:
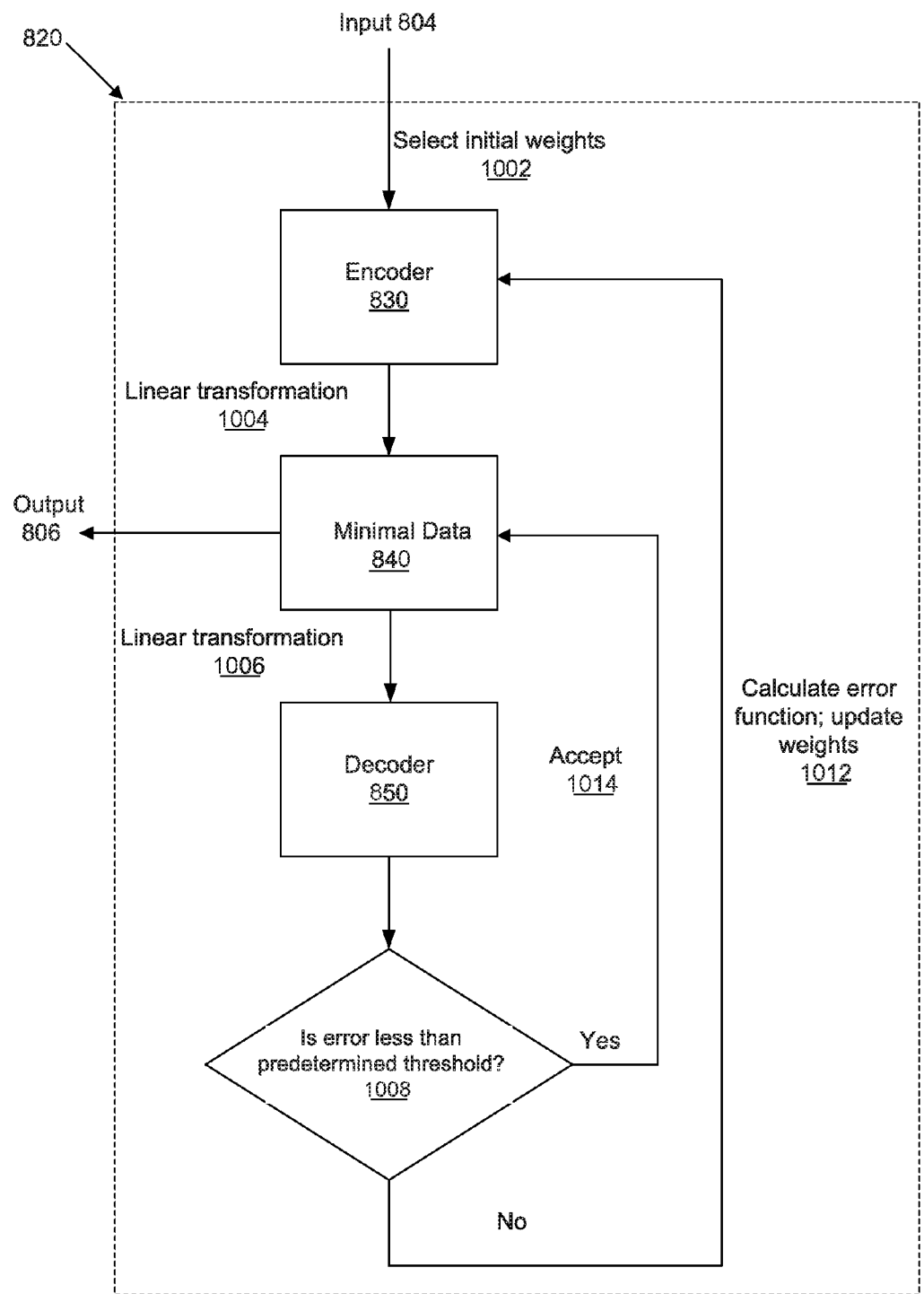
FIG. 10 illustrates a flowchart representing a process by which minimal physiological data may be extracted from the input to an autoencoder.

FIG. 10 illustrates a flowchart representing a process by which minimal physiological data may be extracted from the input to an autoencoder, in accordance with some embodiments. The encoder 830 (of FIG. 9) may accept as input a vectorized set of pre-processed physiological information 804 from the pre-processing module 810 (see FIG. 8). The initial weights 1002 of each node in each layer of the encoder 830, minimal physiological data 840, and decoder 850 may be selected according to any preferred procedure. The encoder may apply a set of linear transformations 1004, one linear transformation at each encoding layer, to calculate a first-pass linear minimal physiological data 840. Each linear transformation at each layer of the encoder may reduce the dimensionality of the information passed to the next layer of the encoder.

The decoder may apply a further set of linear transformations 1006, one linear transformation at each decoding layer. Each linear transformation at each layer of the decoder may increase the dimensionality of the information passed to the next layer of the decoder. The final layer of the decoder may produce a test code given by the weights of the nodes of the final layer of the decoder. The test code may be of the same dimensionality as the input to the decoder.

The values of the test code and the values of the input to the encoder may be compared through an error function in order to calculate an error. The error function may be the L1 error, given by the sum of absolute differences between the test code and the input to the encoder. The error function may be the L2 error or the Euclidean error, given by the sum of the squared differences between the test code and the input to the encoder. The error function may be an LN error, or a generalized Euclidean error of arbitrary dimensionality N. The error function may be any other error function. The error function may be the same for each iteration. The error function may change between successive iterations.

The error calculated from the test code and the input to the encoder may be compared to a condition. The condition may be based on a predetermined threshold. If the error satisfies the condition, the minimal physiological data may be accepted 1014 and the value of the minimal physiological data may be output 806. If the error fails to satisfy the condition, the weights of each node in each layer of the encoder 830, physiological data 840, and decoder 850 may be updated 1014 according to any preferred procedure. At this point, the procedure may proceed iteratively until the condition is satisfied. The condition may be defined such that that the error is smaller than a predetermined threshold value. The condition may also be defined such that the error is the smaller than any one of previously calculated errors. In some embodiments, the condition may remain the same for each iteration. In other embodiments, the condition may change between successive iterations. The procedure and iterations may be configured to end when the condition is met. In some embodiments, when the condition is met, the physiological population data from the current iteration will be output.

Although particular reference is made to autoencoding methods, other machine learning techniques including various supervised machine learning techniques, various semi-supervised machine learning techniques, and/or various unsupervised machine learning techniques may be implemented in the in the machine learning module. The machine learning techniques may be trainable. The machine learning techniques may be trainable by interaction with a human trainer (supervised machine learning), by self-training (unsupervised machine learning), or by a combination of the two (semi-supervised machine learning). For instance, the machine learning module may utilize alternating decision trees (ADTree), Decision Stumps, functional trees (FT), logistic model trees (LMT), logistic regression, Random Forests, linear classifiers, neural networks, sparse dictionaries, Diabolo networks, or any machine learning algorithm or statistical algorithm known in the art. One or more algorithms may be used together to generate an ensemble method, wherein the ensemble method may be optimized using a machine learning ensemble meta-algorithm such as a boosting (e.g., AdaBoost, LPBoost, TotalBoost, BrownBoost, MadaBoost, LogitBoost, etc.) to reduce bias and/or variance. Machine learning analyses may be performed using one or more of many programming languages and platforms known in the art, such as R, Weka, Python, and/or Matlab, for example.

Figure 11:
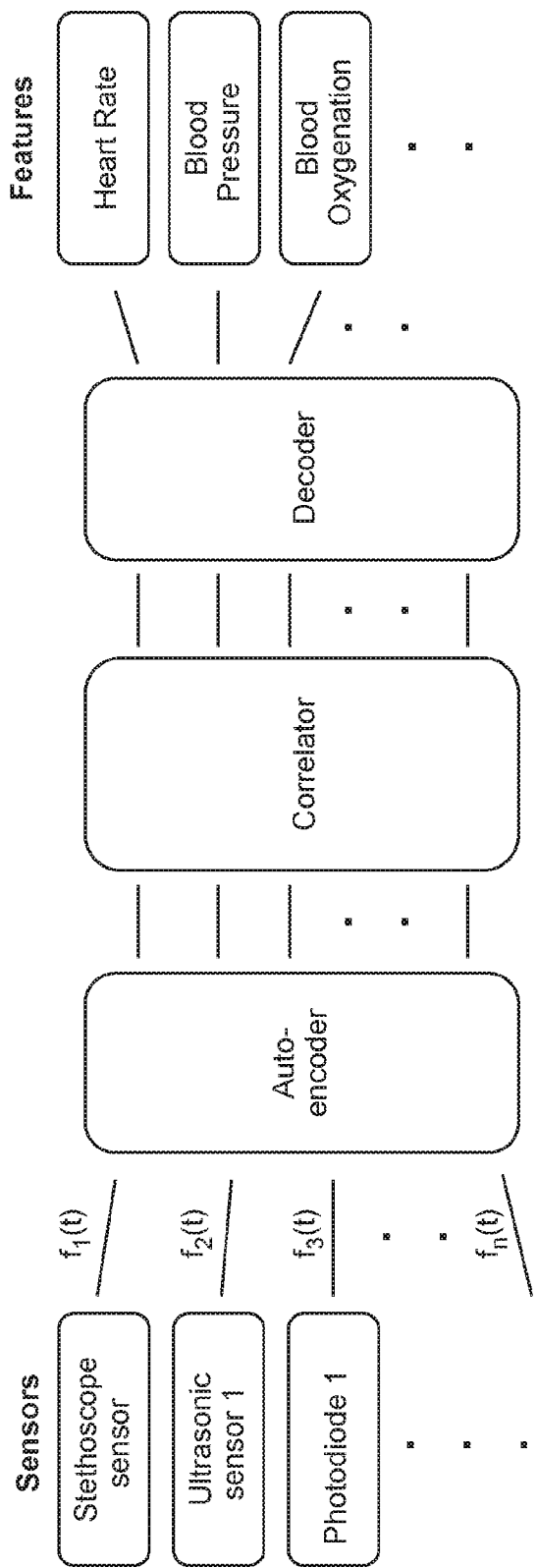
FIG. 11 schematically illustrates a method for extracting features from a stethoscopic audio signal obtained by a mechanical diaphragm, an ultrasonic signal obtained by an ultrasonic transducer, and one or more non-stethoscopic, non-ultrasonic signals obtained by a non-stethoscopic, non-ultrasonic sensor.

FIG. 11 schematically illustrates a method for extracting features from a stethoscopic audio signal obtained by a mechanical diaphragm, an ultrasonic signal obtained by an ultrasonic transducer, and one or more non-stethoscopic, non-ultrasonic signals obtained by a non-stethoscopic, non-ultrasonic sensor. The method may utilize any one of the techniques described herein with respect to FIG. 8, FIG. 9, and FIG. 10 to apply an encoder and decoder to a series of sensor data. The sensor data may comprise a time series of sensor values f1(t) associated with a stethoscope sensor (such as the mechanical diaphragm described herein), a time series of sensor values f2(t) associated with a first ultrasound sensor, a time series of sensor values f3(t) associated with a first photodiode, and so on. In general, the sensor data may comprise n time series of sensor values, where n is a positive integer. Each time series of sensor values may be associated with any one of the stethoscope, ultrasonic, or non-stethoscopic, non-ultrasonic sensors described herein. Each time series may be passed to an autoencoder, progress through a correlator (also referred to as a set of inner layers) and a decoder, and output extracted features. For instance, the autoencoder, correlator, and decoder may output extracted features related to a heart rate, blood pressure, blood oxygenation, or any other clinically relevant feature described herein.

Figure 19:
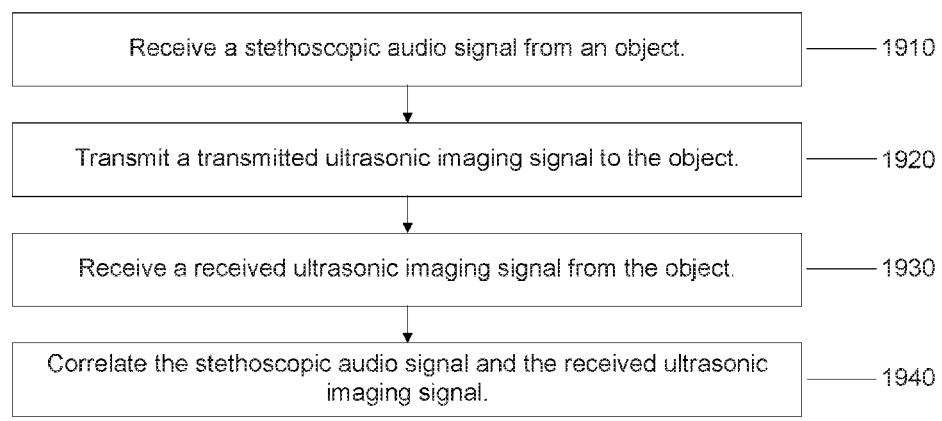
FIG. 19 illustrates a method for receiving a stethoscopic audio signal, transmitting and receiving an ultrasonic imaging signal, and correlating the stethoscopic audio signal and the ultrasonic imaging signal.

FIG. 19 illustrates a method 1900 for receiving a stethoscopic audio signal, transmitting and receiving an ultrasonic imaging signal, and correlating the stethoscopic audio signal and the ultrasonic imaging signal.

In a first operation 1910, a stethoscopic audio signal is received from an object. The stethoscopic audio signal may be received by a stethoscope head comprising a mechanical diaphragm, as described herein.

In a second operation 1920, a transmitted ultrasonic imaging signal is transmitted to the object. The transmitted ultrasonic imaging signal may be transmitted by an ultrasonic transducer, as described herein.

In a third operation 1930, a received ultrasonic imaging signal is received from the object. The received ultrasonic imaging signal may be received by an ultrasonic transducer, as described herein.

In a fourth operation 1940, the stethoscopic audio signal and the received ultrasonic imaging signal are correlated. The stethoscopic audio signal and the received ultrasonic imaging signal may be correlated by a model, as described herein.

The method 1900 may further comprise an operation (not shown in FIG. 19) of detecting a non-stethoscopic, non-ultrasonic signal. The non-stethoscopic, non-ultrasonic signal may be detected by a non-stethoscopic, non-ultrasonic sensor, as described herein.

The method 1900 may be implemented by any of the devices described herein, such as the devices described herein with respect to FIG. 8, FIG. 9, FIG. 10, or FIG. 11.

Many variations, alterations, and adaptations based on the method 1900 provided herein are possible. For example, the order of the operations of the method 1900 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated and some of the operations may be manual.

The stethoscope device described herein may be configured to perform beamsteering of a transmitted ultrasonic imaging signal by interfering a transmitted ultrasonic imaging signal with an audio signal. The stethoscope head may comprise an audio transducer for transmitting an audio signal to a subject. The stethoscope head may comprise an interference circuit for interfering a transmitted ultrasonic imaging signal with the audio signal. The interference circuit may steer the ultrasonic imaging signal to an object. The audio transducer or interference circuit may be detachably coupled to a housing of the stethoscope head. The audio transducer or interference circuit may be physically coupled to a housing of the stethoscope head. The audio transducer or interference circuit may be functionally coupled to a housing of the stethoscope head.

The interference circuit may interfere the transmitted ultrasonic imaging signal with the audio signal based on a model of the object's response to the audio signal. The model may be similar to any model described herein. The model may correlate the ultrasonic imaging signal with the audio signal to generate an extracted feature parameter. The model may correlate the ultrasonic signal with the audio signal by convolving the ultrasonic and audio signals with first and second weighting functions, respectively, to form weighted ultrasonic and weighted audio signals, respectively. The weighted ultrasonic and weighted audio signals may be correlated by performing auto-correlation or cross-correlation on the weighted signals. The model may correlate the ultrasonic signal with the audio signal by transforming (as by an integral Fourier transform, Fourier series transform, Z-transform, wavelet transform, cosine series transform, sine series transform, Taylor series transform, Laurent series transform, Laplace transform, Hadamard transform, or any other mathematical transform) the ultrasonic and audio signals to form transformed ultrasonic and transformed audio signals, respectively. The transformed ultrasonic and transformed audio signals may be correlated by performing auto-correlation or cross-correlation on the transformed signals. The model may correlated the ultrasonic signal and audio signal by encoding and mapping the ultrasonic and audio signals to a set of features using a machine learning technique. The machine learning technique may be a neural network, sparse dictionary, Diabolo network, or any other machine learning technique described herein.

Figure 20:
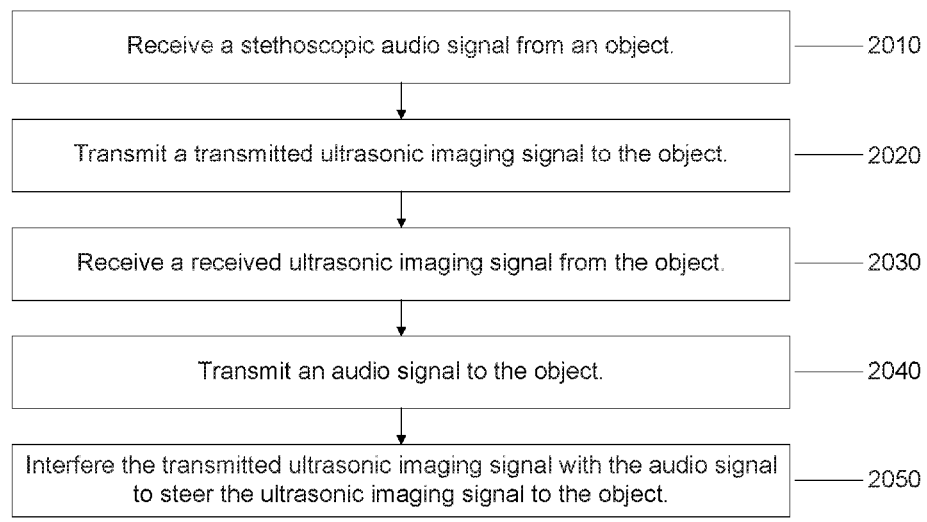
FIG. 20 illustrates a method for receiving a stethoscopic audio signal, transmitting and receiving an ultrasonic imaging signal, transmitting an audio signal, and interfering the transmitted ultrasonic imaging signal and the audio signal to steer the ultrasonic imaging signal.

FIG. 20 illustrates a method 2000 for receiving a stethoscopic audio signal, transmitting and receiving an ultrasonic imaging signal, transmitting an audio signal, and interfering the transmitted ultrasonic imaging signal and the audio signal to steer the ultrasonic imaging signal.

In a first operation 2010, a stethoscopic audio signal is received from an object. The stethoscopic audio signal may be received by a stethoscope head comprising a mechanical diaphragm, as described herein.

In a second operation 2020, a transmitted ultrasonic imaging signal is transmitted to the object. The transmitted ultrasonic imaging signal may be transmitted by an ultrasonic transducer, as described herein.

In a third operation 2030, a received ultrasonic imaging signal is received from the object. The received ultrasonic imaging signal may be received by an ultrasonic transducer, as described herein.

In a fourth operation 2040, an audio signal is transmitted to the object. The audio signal may be transmitted by an audio transducer, as described herein.

In a fifth operation 2050, transmitted ultrasonic imaging signal is interfered with the audio signal to steer the ultrasonic imaging signal. The transmitted ultrasonic imaging signal and the audio signal may be interfered by an interference circuit, as described herein.

The method 2000 may further comprise an operation (not shown in FIG. 20) of detecting a non-stethoscopic, non-ultrasonic signal. The non-stethoscopic, non-ultrasonic signal may be detected by a non-stethoscopic, non-ultrasonic sensor, as described herein.

The method 2000 may be implemented by any of the devices described herein.

Many variations, alterations, and adaptations based on the method 2000 provided herein are possible. For example, the order of the operations of the method 2000 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated and some of the operations may be manual.

Figure 12:
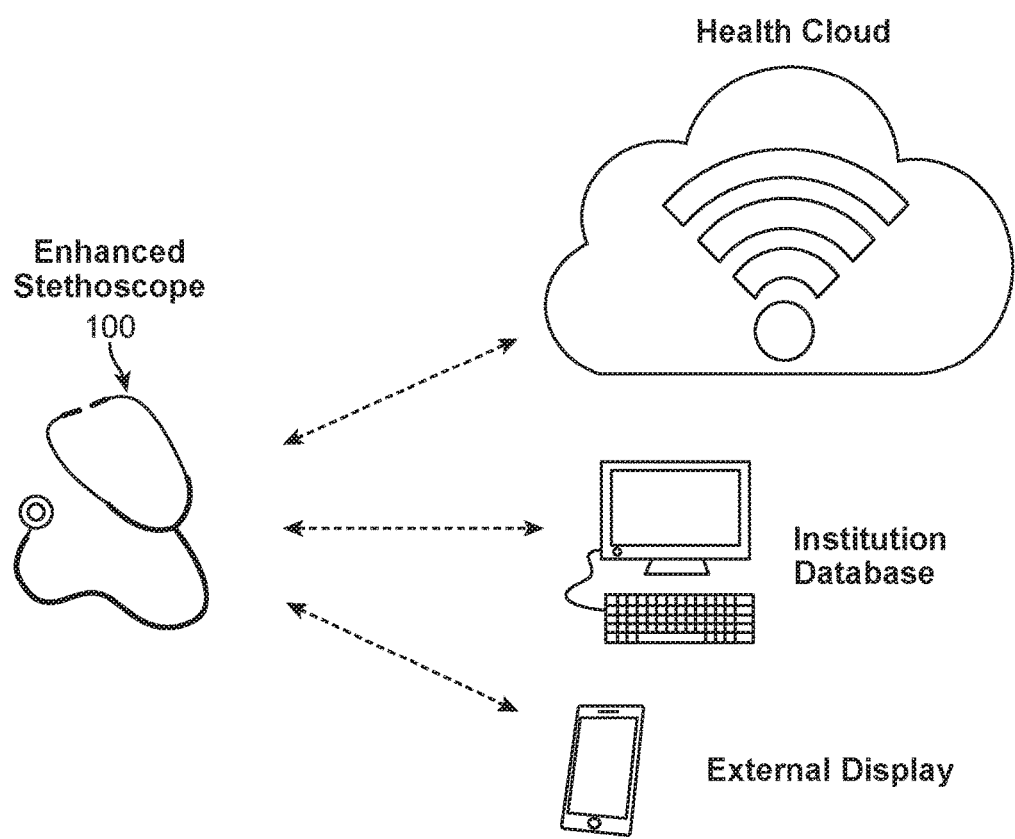
FIG. 12 shows how information from the stethoscope device may be transmitted to information systems.

FIG. 12 shows how information from the stethoscope device 100 may be transmitted to information systems. As described herein, the stethoscope device may have the ability to transmit or receive information. The stethoscope device may transmit information, such as the sensor data or extracted features, to a variety of information systems. The information may be transmitted to an external display for easy visualization, stored in an institutional database (such as a database associated with a doctor's office, hospital, or network of offices or hospitals), or to a cloud-based health system. The information may thus be accessed by institutions that have an interest in the information.

Figure 13:
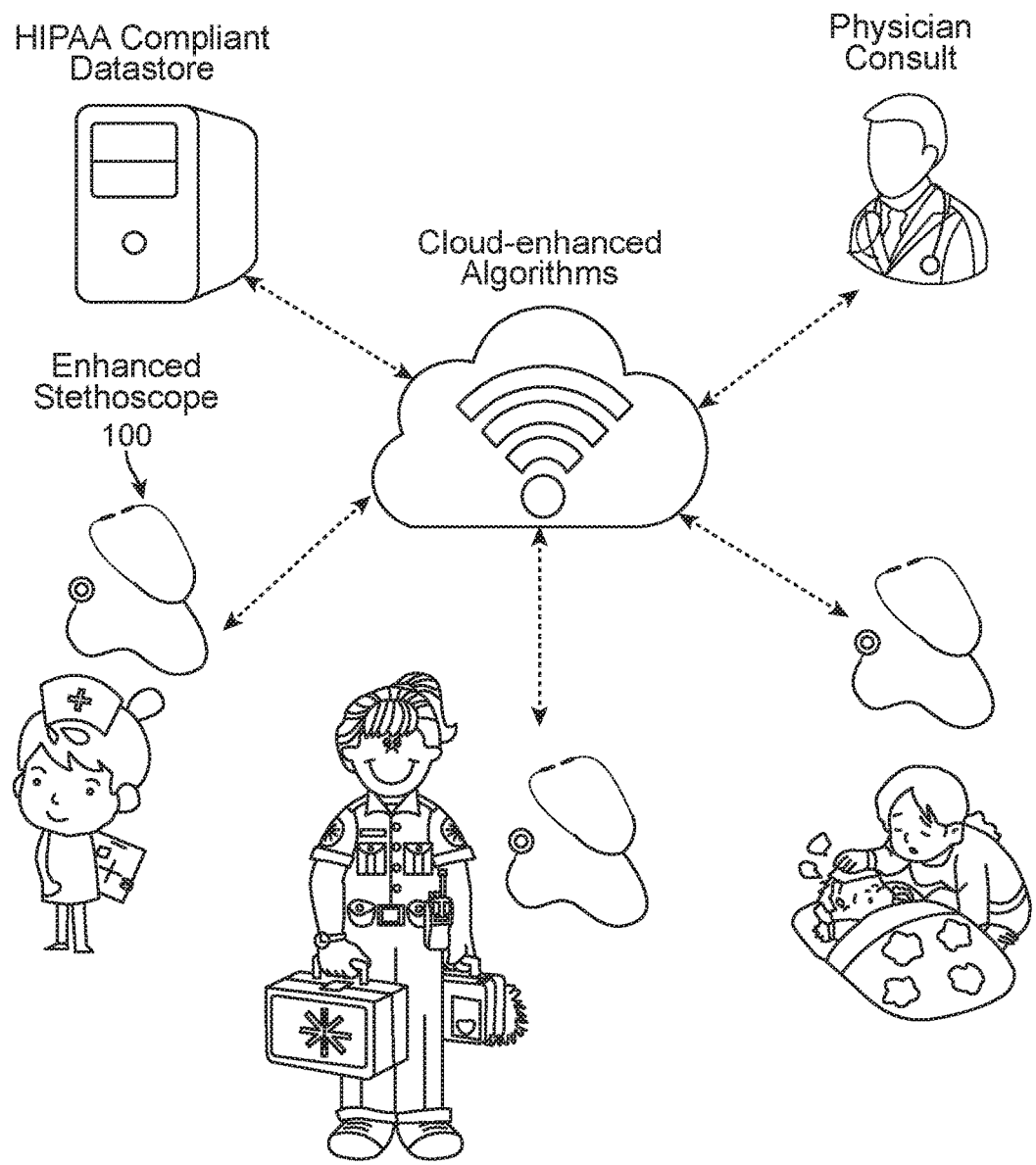
FIG. 13 shows how information from the stethoscope device may be utilized by different individuals or institutions.

FIG. 13 shows how information from the stethoscope device 100 may be utilized by different individuals or institutions. The information from the stethoscope device may be transmitted to a cloud server. The cloud server may apply algorithms to the information. The information may be stored in a Health Insurance Portability and Accountability (HIPAA) Act-compliant database. The information may be accessed by a nurse, a physician (such as a consulting physician), an emergency medical technician, or another medical professional. The information may be accessed by a parent of a patient, for instance.

Digital Processing Device

The systems, apparatus, and methods described herein may include a digital processing device, or use of the same. The digital processing device may include one or more hardware central processing units (CPU) that carry out the device's functions. The digital processing device may further comprise an operating system configured to perform executable instructions. In some instances, the digital processing device is optionally connected to a computer network, is optionally connected to the Internet such that it accesses the World Wide Web, or is optionally connected to a cloud computing infrastructure. In other instances, the digital processing device is optionally connected to an intranet. In other instances, the digital processing device is optionally connected to a data storage device.

In accordance with the description herein, suitable digital processing devices may include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers may include those with booklet, slate, and convertible configurations, known to those of skill in the art.

The digital processing device may include an operating system configured to perform executable instructions. The operating system may be, for example, software, including programs and data, which may manage the device's hardware and provides services for execution of applications. Those of skill in the art will recognize that suitable server operating systems may include, by way of non-limiting examples, FreeBSD, OpenBSD, NetBSD®, Linux, Apple® Mac OS XServer®, Oracle® Solaris®, WindowsServer®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some cases, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, GoogleTV®, GoogleChromecast®, AmazonFire®, and Samsung® HomeSync®. Those of skill in the art will also recognize that suitable video game console operating systems include, by way of non-limiting examples, Sony® P53®, Sony® P54®, Microsoft® Xbox 360®, Microsoft Xbox One, Nintendo® Wii®, Nintendo® Wii U®, and Ouya®.

In some instances, the device may include a storage and/or memory device. The storage and/or memory device may be one or more physical apparatuses used to store data or programs on a temporary or permanent basis. In some instances, the device is volatile memory and requires power to maintain stored information. In other instances, the device is non-volatile memory and retains stored information when the digital processing device is not powered. In still other instances, the non-volatile memory comprises flash memory. The non-volatile memory may comprise dynamic random-access memory (DRAM). The non-volatile memory may comprise ferroelectric random access memory (FRAM). The non-volatile memory may comprise phase-change random access memory (PRAM). The device may be a storage device including, by way of non-limiting examples, CD-ROMs, DVDs, flash memory devices, magnetic disk drives, magnetic tapes drives, optical disk drives, and cloud computing based storage. The storage and/or memory device may also be a combination of devices such as those disclosed herein.

The digital processing device may include a display to send visual information to a user. The display may be a cathode ray tube (CRT). The display may be a liquid crystal display (LCD). Alternatively, the display may be a thin film transistor liquid crystal display (TFT-LCD). The display may further be an organic light emitting diode (OLED) display. In various cases, on OLED display is a passive-matrix OLED (PMOLED) or active-matrix OLED (AMO-LED) display. The display may be a plasma display. The display may be a video projector. The display may be a combination of devices such as those disclosed herein.

The digital processing device may also include an input device to receive information from a user. For example, the input device may be a keyboard. The input device may be a pointing device including, by way of non-limiting examples, a mouse, trackball, track pad, joystick, game controller, or stylus. The input device may be a touch screen or a multi-touch screen. The input device may be a microphone to capture voice or other sound input. The input device may be a video camera or other sensor to capture motion or visual input. Alternatively, the input device may be a Kinect™, Leap Motion™, or the like. In further aspects, the input device may be a combination of devices such as those disclosed herein.

Non-Transitory Computer Readable Storage Medium

In some instances, the systems, apparatus, and methods disclosed herein may include one or more non-transitory computer readable storage media encoded with a program including instructions executable by the operating system of an optionally networked digital processing device. In further instances, a computer readable storage medium is a tangible component of a digital processing device. In still further instances, a computer readable storage medium is optionally removable from a digital processing device. A computer readable storage medium may include, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

The systems, apparatus, and methods disclosed herein may include at least one computer program, or use of the same. A computer program includes a sequence of instructions, executable in the digital processing device's CPU, written to perform a specified task. In some embodiments, computer readable instructions are implemented as program modules, such as functions, objects, Application Programming Interfaces (APIs), data structures, and the like, that perform particular tasks or implement particular abstract data types. In light of the disclosure provided herein, those of skill in the art will recognize that a computer program, in certain embodiments, is written in various versions of various languages.

The functionality of the computer readable instructions may be combined or distributed as desired in various environments. A computer program may comprise one sequence of instructions. A computer program may comprise a plurality of sequences of instructions. In some instances, a computer program is provided from one location. In other instances, a computer program is provided from a plurality of locations. In additional cases, a computer program includes one or more software modules. Sometimes, a computer program may include, in part or in whole, one or more web applications, one or more mobile applications, one or more standalone applications, one or more web browser plug-ins, extensions, add-ins, or add-ons, or combinations thereof.

Web Application

A computer program may include a web application. In light of the disclosure provided herein, those of skill in the art will recognize that a web application, in various aspects, utilizes one or more software frameworks and one or more database systems. In some cases, a web application is created upon a software framework such as Microsoft® .NET or Ruby on Rails (RoR). In some cases, a web application utilizes one or more database systems including, by way of non-limiting examples, relational, non-relational, object oriented, associative, and XML database systems. Sometimes, suitable relational database systems may include, by way of non-limiting examples, Microsoft® SQL Server, mySQL™, and Oracle®. Those of skill in the art will also recognize that a web application, in various instances, is written in one or more versions of one or more languages. A web application may be written in one or more markup languages, presentation definition languages, client-side scripting languages, server-side coding languages, database query languages, or combinations thereof. A web application may be written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). A web application may be written to some extent in a client-side scripting language such as Asynchronous Javascript and XML (AJAX), Flash® Actionscript, Javascript, or Silverlight®. A web application may be written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. Sometimes, a web application may be written to some extent in a database query language such as Structured Query Language (SQL). Other times, a web application may integrate enterprise server products such as IBM® Lotus Domino®. In some instances, a web application includes a media player element. In various further instances, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

A computer program may include a mobile application provided to a mobile digital processing device. In some cases, the mobile application is provided to a mobile digital processing device at the time it is manufactured. In other cases, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

A computer program may include a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™ Lisp, Python™, Visual Basic, and VB .NET, or combinations thereof. Compilation is often performed, at least in part, to create an executable program. A computer program may include one or more executable complied applications.

Web Browser Plug-in

The computer program may include a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) may be software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The systems and methods disclosed herein may include software, server, and/or database modules, or use of the same. In view of the disclosure provided herein, software modules may be created by techniques known to those of skill in the art using machines, software, and languages known to the art. The software modules disclosed herein may be implemented in a multitude of ways. A software module may comprise a file, a section of code, a programming object, a programming structure, or combinations thereof. A software module may comprise a plurality of files, a plurality of sections of code, a plurality of programming objects, a plurality of programming structures, or combinations thereof. In various aspects, the one or more software modules comprise, by way of non-limiting examples, a web application, a mobile application, and a standalone application. In some instances, software modules are in one computer program or application. In other instances, software modules are in more than one computer program or application. In some cases, software modules are hosted on one machine. In other cases, software modules are hosted on more than one machine. Sometimes, software modules may be hosted on cloud computing platforms. Other times, software modules may be hosted on one or more machines in one location. In additional cases, software modules are hosted on one or more machines in more than one location.

Databases

The methods, apparatus, and systems disclosed herein may include one or more databases, or use of the same. In view of the disclosure provided herein, those of skill in the art will recognize that many databases are suitable for storage and retrieval of analytical information described elsewhere herein. In various aspects described herein, suitable databases may include, by way of non-limiting examples, relational databases, non-relational databases, object oriented databases, object databases, entity-relationship model databases, associative databases, and XML databases. A database may be internet-based. A database may be web-based. A database may be cloud computing-based. Alternatively, a database may be based on one or more local computer storage devices.

Services

Methods and systems described herein may further be performed as a service. For example, a service provider may obtain a sample that a customer wishes to analyze. The service provider may then encodes the sample to be analyzed by any one of the methods described herein, performs the analysis and provides a report to the customer. The customer may also perform the analysis and provides the results to the service provider for decoding. In some instances, the service provider then provides the decoded results to the customer. In other instances, the customer may receive encoded analysis of the samples from the provider and decodes the results by interacting with softwares installed locally (at the customer's location) or remotely (e.g. on a server reachable through a network). Sometimes, the softwares may generate a report and transmit the report to the costumer. Exemplary customers include clinical laboratories, hospitals, industrial manufacturers and the like. Sometimes, a customer or party may be any suitable customer or party with a need or desire to use the methods provided herein.

Server

Figure 14:
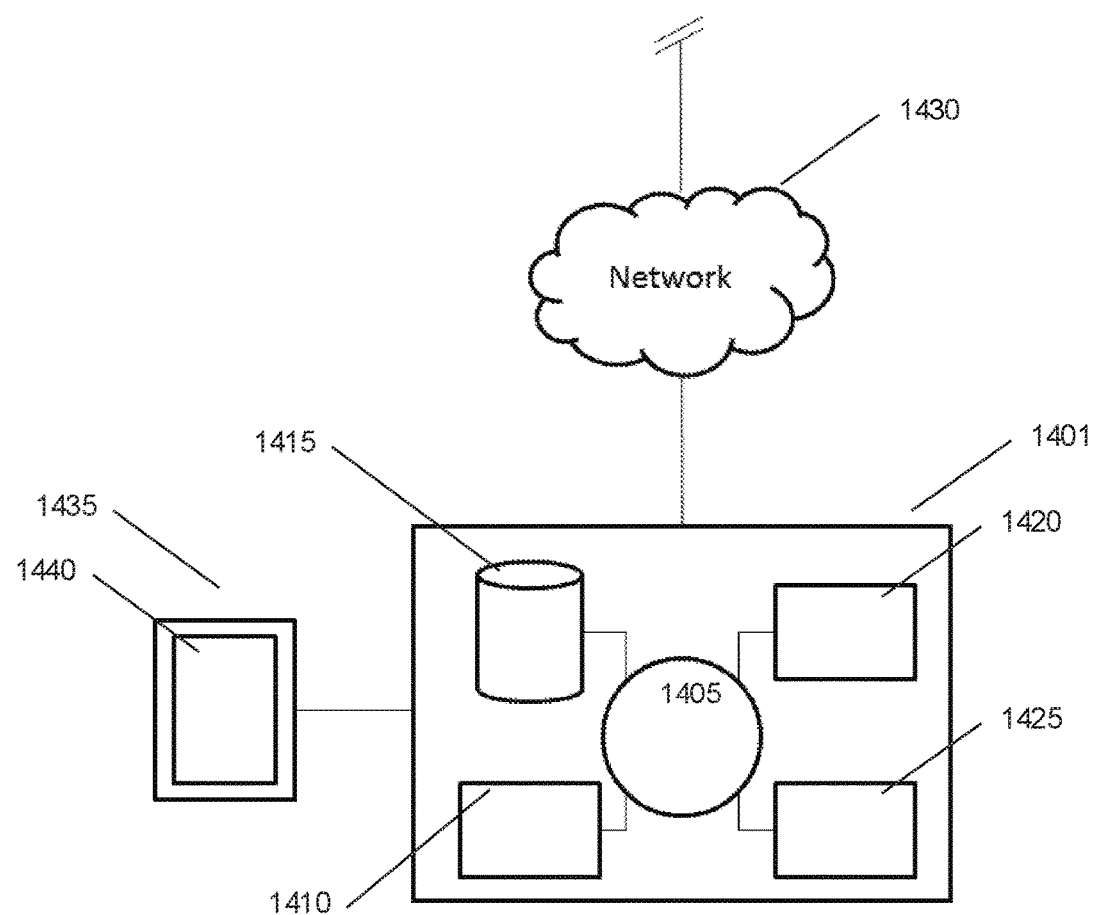
FIG. 14 shows an exemplary digital processing device programmed or otherwise configured to operate the stethoscope devices and methods described herein.

The methods provided herein may be processed on a server or a computer server, as shown in FIG. 14). The server 1401 may include a central processing unit (CPU, also "processor") 1405 which may be a single core processor, a multi core processor, or plurality of processors for parallel processing. A processor used as part of a control assembly may be a microprocessor. The server 1401 may also include memory 1410 (e.g. random access memory, read-only memory, flash memory); electronic storage unit 1415 (e.g. hard disk); communications interface 1420 (e.g. network adaptor) for communicating with one or more other systems; and peripheral devices 1425 which includes cache, other memory, data storage, and/or electronic display adaptors. The memory 1410, storage unit 1415, interface 1420, and peripheral devices 1425 may be in communication with the processor 1405 through a communications bus (solid lines), such as a motherboard. The storage unit 1415 may be a data storage unit for storing data. The server 1401 may be operatively coupled to a computer network ("network") 1430 with the aid of the communications interface 1420. A processor with the aid of additional hardware may also be operatively coupled to a network. The network 1430 may be the Internet, an intranet and/or an extranet, an intranet and/or extranet that is in communication with the Internet, a telecommunication or data network. The network 1430 with the aid of the server 1401, may implement a peer-to-peer network, which may enable devices coupled to the server 1401 to behave as a client or a server. The server may be capable of transmitting and receiving computer-readable instructions (e.g., device/system operation protocols or parameters) or data (e.g., sensor measurements, analysis of sensor measurements, etc.) via electronic signals transported through the network 1430. Moreover, a network may be used, for example, to transmit or receive data across an international border.

The server 1401 may be in communication with one or more output devices 1435 such as a display or printer, and/or with one or more input devices 1440 such as, for example, a keyboard, mouse, or joystick. The display may be a touch screen display, in which case it functions as both a display device and an input device. Different and/or additional input devices may be present such an enunciator, a speaker, or a microphone. The server may use any one of a variety of operating systems, such as for example, any one of several versions of Windows®, or of MacOS®, or of Unix®, or of Linux®.

The storage unit 1415 may store files or data associated with the operation of a device, systems or methods described herein.

The server may communicate with one or more remote computer systems through the network 1430. The one or more remote computer systems may include, for example, personal computers, laptops, tablets, telephones, Smart phones, or personal digital assistants.

A control assembly may include a single server 1401. In other situations, the system may include multiple servers in communication with one another through an intranet, extranet and/or the Internet.

The server 1401 may be adapted to store device operation parameters, protocols, methods described herein, and other information of potential relevance. Such information may be stored on the storage unit 1415 or the server 1401 and such data is transmitted through a network.

EXAMPLES

The devices and methods described herein may be used to obtain a variety of information from a sample. The sample may be a living sample, such as a human or a non-human animal subject, such as non-human primates, horses, livestock such as bovines or sheep, dogs, cats, birds, mice, or any other animal. The systems and methods described herein may be used to detect or diagnose a variety of health conditions in a human or non-human subject. For instance, the systems and methods may be used to detect injuries or conditions associated with one or more of the brain, heart, lungs, stomach, small intestine, large intestine, liver, kidney, colon, or any other internal organ of a human or non-human subject. The systems and methods may be used to detect injuries or conditions associated with one or more of a bone (such as a broken bone), connective tissue (such as a cartilage tear), or blood vessel (such as an aneurysm).

The devices and methods described herein may be utilized to determine the presence of tumors, fractured bones, ruptured vasculature, lacerated organs, or free abdominal fluid within a human or non-human subject. Furthermore, the devices and methods may be utilzied to identify any of the following conditions in a human or non-human subject: venipuncture, central line placement, gallstones, pneumothorax, pleural effusion, pneumonia, cardiac function, pericardial effusion, cardiac tamponade, bladder volume, bowel obstruction, organ structure functional abnormalities, peritonsillar abscess, superficial or deep space abscess, cellulitis, fluid status, inferior vena cava collapse, carotid intimal thickness, carotid artery dissection, abdominal aortic aneurysm, aortic dissection, and pregnancy.

Figure 15:
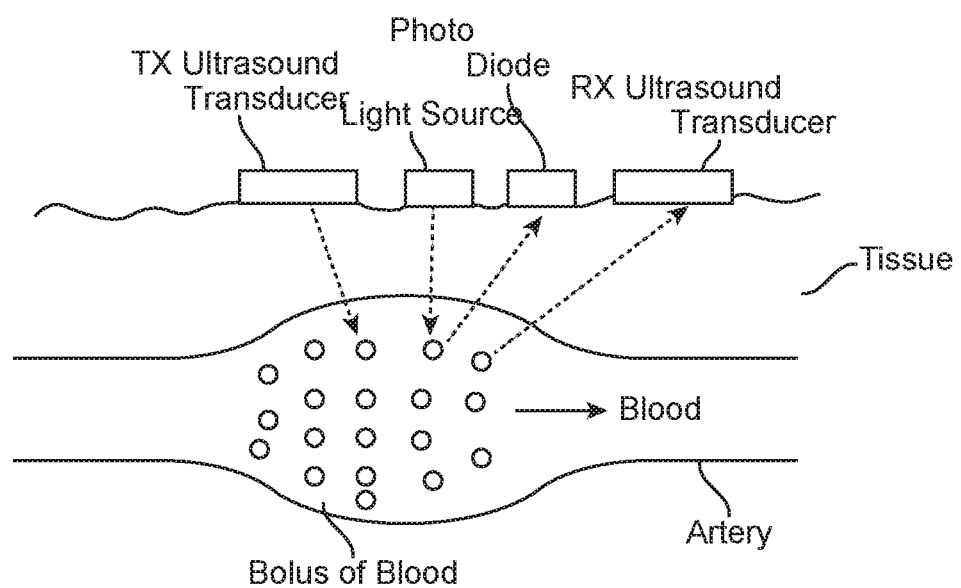
FIG. 15 depicts the use of an enhanced stethoscope device for monitoring blood pressure.

FIG. 15 depicts the use of an enhanced stethoscope device for monitoring blood pressure. The stethoscope device may be any stethoscope device described herein. In particular, the stethoscope device may comprise a first ultrasonic transducer, a light source, and a light detector. The stethoscope device may optionally comprise a second ultrasonic transducer. The first ultrasonic transducer may operate in a Tx mode. The second ultrasonic transducer may operate in a receive mode. The stethoscope device may be placed above the skin of a subject (such as skin in a subject's arm). As a bolus of blood travels through an artery beneath the skin of the subject, the stethoscope device may transmit an ultrasonic signal from the first ultrasonic transducer and an optical signal from the light source. The ultrasonic signal or the optical signal may be scattered, dispersed, or reflected from the bolus. The scattered, dispersed, or reflected ultrasonic signal or optical signal may be detector by the second ultrasonic transducer or the light detector, respectively. The intensity of the scattered, dispersed, or reflected ultrasonic signal or optical signal may be compared to the intensity of the transmitted ultrasonic signal or the transmitted optical signal, respectively. These measurements may yield a velocity of the blood bolus as measured by the ultrasonic imaging signal and the optical signal, respectively. The velocity of the blood bolus as measured by the ultrasonic imaging signal may be normalized by the velocity of the blood bolus as measured by the optical signal, or vice versa. These values may be synthesized and correlated to determine one or more physiometric parameters of the subject, such as the subject's heart rate, blood pressure, or respiration, as described herein with respect to FIG. 16.

Figure 16:
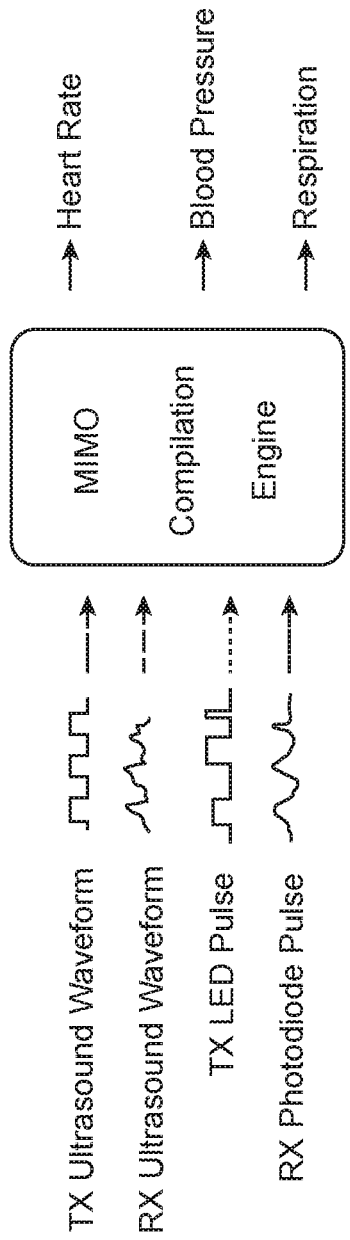
FIG. 16 illustrates a multi-input multi-output (MIMO) correlation for determining a physiometric parameter associated with ultrasonic and optical measurement of a blood bolus.

FIG. 16 illustrates a multi-input multi-output (MIMO) correlation for determining a physiometric parameter associated with ultrasonic and optical measurement of a blood bolus. The MIMO correlation may utilize any of the modeling techniques described herein, such as any machine learning or statistical model described herein. The MIMO correlation may produce a unique correlation between the ultrasonic imaging signal and the optical signal. The unique correlation may allow for the extraction of any physiometric information described herein. The MIMO correlation may allow for the extraction of signals that may otherwise be obfuscated by noise.

The devices and methods described herein may be utilized for applications in fields outside of the medical fields described above. For instance, the devices and methods may be used to provide information about the internal conditions of mechanical systems, such as the engines or transmissions of vehicles. The stethoscope functionality may be used to detect abnormalities in the mechanical processes of an engine or transmission. The ultrasonic functionality may be used to image the engine or transmission to determine if it has sustained internal damage. The non-stethoscopic, non-ultrasonic sensors may provide additional information about the state of the engine or transmission, such as its temperature.

The devices and methods may be used for non-destructive testing of infrastructure.

For instance, the devices and methods may be used to examine the internal structure of concrete (in streets or highways, bridges, buildings, or other structures) to determine whether the concrete or metal rebar within the concrete has been damaged. The devices and methods may be used to examine the internal structures of pipelines to determine whether they are damaged and may represent a threat to life, property, or the environment.

The devices and methods described herein may be utilized to examine the internal structures of other building materials, such as stone, brick, wood, sheetrock, thermal insulating, plastic piping, polyvinyl chloride (PVC) piping, fiberglass, or paint.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A stethoscope device comprising:
   a stethoscope head comprising a mechanical diaphragm for receiving a stethoscopic audio signal from an object;
   a first ultrasonic transducer for transmitting a first transmitted ultrasonic imaging signal to the object at a first frequency and receiving a first received ultrasonic imaging signal from the object at the first frequency; and
   a second ultrasonic transducer for transmitting a second transmitted ultrasonic imaging signal to the object at a second frequency different from the first frequency and receiving a second received ultrasonic imaging signal from the object at the second frequency, wherein
   the first and second ultrasonic transducers transmit and receive simultaneously with one another.

2. The stethoscope device of claim 1, wherein the frequency of the first transmitted ultrasonic imaging signal is selected from the group consisting of: 100 kHz, 200 kHz, 300 kHz, 400 kHz, 500 kHz, 650 kHz, 700 kHz, 800 kHz, 850 kHz, 900 kHz, 1 MHz, 2 MHz, 3 MHz, 5.5 MHz, 6 MHz, 8 MHz, and 11 MHz; and the frequency of the second transmitted ultrasonic imaging signal is in the frequency range of 0.5 MHz-30 MHz.

3. The stethoscope device of claim 1, wherein the frequency of the first received ultrasonic imaging signal is selected from the group consisting of: 100 kHz, 200 kHz, 300 kHz, 400 kHz, 500 kHz, 650 kHz, 700 kHz, 800 kHz, 850 kHz, 900 kHz, 1 MHz, 2 MHz, 3 MHz, 5.5 MHz, 6 MHz, 8 MHz, and 11 MHz; and the frequency of the second received ultrasonic imaging signal is in the frequency range of 0.5 MHz-30 MHz.

4. The stethoscope device of claim 1, wherein the frequency of the first transmitted ultrasonic imaging signal is in the frequency range of 0.5 MHz-30 MHz and the frequency of the second transmitted ultrasonic imaging signal is in the frequency range of 0.5 MHz-30 MHz and is distinct from the frequency of the first transmitted ultrasonic imaging signal.

5. The stethoscope device of claim 1, wherein the frequency of the first received ultrasonic imaging signal is in the frequency range of 0.5 MHz-30 MHz and the frequency of the second received ultrasonic imaging signal is in the frequency range of 0.5 MHz-30 MHz and is distinct from the frequency of the first received ultrasonic imaging signal.

6. The stethoscope device of claim 1, wherein the first received ultrasonic imaging signal is normalized by the second received ultrasonic imaging signal.

7. The stethoscope device of claim 1, wherein the frequency of the first received ultrasonic imaging signal is in the frequency range of 0.5 MHz-30 MHz and the frequency of the second received ultrasonic imaging signal is in the frequency range of 0.5 MHz-30 MHz and is distinct from the frequency of the first received ultrasonic imaging signal.

8. The stethoscope device of claim 1, wherein the first ultrasonic transducer comprises an element selected from the group consisting of: a lead zirconate titanate (PZT) element, a polyvinylidine fluoride (PVDF) element, a piezoelectric micromachined ultrasound transducer (PMUT) element, and a capacitive micromachined ultrasonic transducer (CMUT) element; and the second ultrasonic transducer comprises an element selected from the group consisting of: a PZT element, a PVDF element, a PMUT element, and a CMUT element.

9. The stethoscope device of claim 1, wherein the first ultrasonic transducer has a bandwidth that partially overlaps with the bandwidth of at least one other ultrasonic imaging sensor.

10. The stethoscope device of claim 1, further comprising a housing coupled to one or more of the stethoscope head, the first ultrasonic transducer, and the second ultrasonic transducer.

11. The stethoscope device of claim 10, wherein one or more of the stethoscope head, the first ultrasonic transducer, and the second ultrasonic transducer is detachably coupled to the housing.

12. The stethoscope device of claim 10, wherein one or more of the stethoscope head, the first ultrasonic transducer, and the second ultrasonic transducer is physically coupled to the housing.

13. The stethoscope device of claim 10, wherein one or more of the stethoscope head, the first ultrasonic transducer, and the second ultrasonic transducer is functionally coupled to the housing.

14. The stethoscope device of claim 1, further comprising: a non-stethoscopic, non-ultrasonic sensor for detecting a non-stethoscopic, non-ultrasonic signal.

15. The stethoscope device of claim 14, wherein the non-stethoscopic, non-ultrasonic sensor is selected from the group consisting of: a non-stethoscopic audio sensor, a temperature sensor, an optical sensor, an electrical sensor, and an electrochemical sensor.

16. The stethoscope device of claim 14, wherein the non-stethoscopic, non-ultrasonic sensor is configured to detect a signal originating from the group consisting of: a body temperature, a respiration rate, a respiration quality, a respiration pathology, a blood pressure level, a blood glucose concentration level, a blood gas concentration level, and a blood oxygenation saturation ($spO_2$) level.

17. The stethoscope device of claim 1, wherein the stethoscope head is functionally coupled to the first and second ultrasonic transducers.

18. The stethoscope device of claim 1, further comprising a battery.

19. The stethoscope device of claim 1, further comprising a power connector for receiving electrical power.

20. The stethoscope device of claim 1, further comprising an inductive power coil for receiving electrical power.

21. The stethoscope device of claim 1, further comprising an inductive power coil for transmitting and receiving data.

22. The stethoscope device of claim 14, further comprising a control for operating the device in one or more of a stethoscopic mode, an ultrasonic imaging mode, or a non-stethoscopic, non-ultrasonic mode.

23. The stethoscope device of claim 22, wherein the control comprises a user interface.

24. The stethoscope device of claim 23, wherein the user interface is configured to provide a user with feedback based on the stethoscopic signal, the ultrasonic signal, or the non-stethoscopic, non-ultrasonic signal.

25. The stethoscope device of claim 24, wherein the user interface comprises a touchscreen device.

26. The stethoscope device of claim 25, further comprising a wireless networking modality.

27. The stethoscope device of claim 26, wherein the wireless networking modality is configured to communicate the stethoscopic audio signal, received ultrasonic signal, or non-stethoscopic, non-ultrasonic signal to a peripheral device.

28. The stethoscope device of claim 27, further comprising a microphone and speaker.

29. The stethoscope device of claim 28, wherein the microphone and speaker enable communication between an operator of the stethoscope device and the stethoscope device.

* * * * *